(12) United States Patent
Tompa Majcen

(10) Patent No.: US 12,268,766 B2
(45) Date of Patent: Apr. 8, 2025

(54) FORMULATIONS CONTAINING ACTIVE OXYGEN COMPOUNDS AND DEVICES FOR APPLICATION THEREOF

(71) Applicant: Dominika Tompa Majcen, Ljubljana (SI)

(72) Inventor: Dominika Tompa Majcen, Ljubljana (SI)

( * ) Notice: Subject to any disclaimer, the term of this patent is extended or adjusted under 35 U.S.C. 154(b) by 0 days.

(21) Appl. No.: 17/422,728

(22) PCT Filed: Jan. 14, 2020

(86) PCT No.: PCT/IB2020/050257
§ 371 (c)(1),
(2) Date: Jul. 13, 2021

(87) PCT Pub. No.: WO2020/148642
PCT Pub. Date: Jul. 23, 2020

(65) Prior Publication Data
US 2022/0062124 A1 Mar. 3, 2022

(30) Foreign Application Priority Data
Jan. 14, 2019 (SI) .................................. P-201900011

(51) Int. Cl.
*A61K 8/22* (2006.01)
*A61K 8/14* (2006.01)
(Continued)

(52) U.S. Cl.
CPC .................. *A61K 8/22* (2013.01); *A61K 8/14* (2013.01); *A61K 8/345* (2013.01); *A61K 8/42* (2013.01);
(Continued)

(58) Field of Classification Search
CPC .......... A61Q 19/00; A61Q 11/00; A61Q 3/00; A61K 8/9789; A61K 8/19; A61K 8/735;
(Continued)

(56) References Cited

U.S. PATENT DOCUMENTS

| 4,826,681 A | 5/1989 | Jacquet et al. |
| 8,802,061 B2 * | 8/2014 | Tichy ..................... A61K 45/06 424/53 |

(Continued)

FOREIGN PATENT DOCUMENTS

| CN | 104837470 A | * 8/2015 | ............... A61K 8/22 |
| DE | 102007050767 | * 8/2008 | |

(Continued)

OTHER PUBLICATIONS

Ren et al., Liposomal delivery of horseradish peroxidase for thermally triggered injectable hyaluronic acid-tyramine hydrogel scaffolds. , Journal of Materials Chemistry B, vol. 3, pp. 4663-4670. (Year: 2015).*

(Continued)

*Primary Examiner* — Lezah Roberts
(74) *Attorney, Agent, or Firm* — Bryant J. Keller; Kirton McConkie

(57) ABSTRACT

The present invention relates to formulations with active oxygen compounds that include active oxygen and other active ingredients for the purposes of care for and/or maintaining and preserving a healthy condition of skin and integumentary systems on the surface of the body of the organism and in the ears, healthy condition of finger- and toenails and of oral cavity, including its mucous membranes, teeth, interdental spaces and periodontal tissues (gingiva) in the oral cavity, i.e. the target areas of the organism. The formulation for skin and integumentary systems on the surface of the body and in the ears and for the finger- and (Continued)

toenails is in the form of a solution, gel, emulsion, lotion, milk, spray, cream, film dressing, liposomes and/or mycelia. The formulation for the oral cavity and related systems and structures, including teeth, interdental spaces and periodontal tissues (gingiva) is in the form of a solution, mouthwash, spray, gel, paste, emulsion, film dressing, liposomes and/or mycelia. These formulations are included in the device for its application on and/or into the said area of the organism.

26 Claims, 9 Drawing Sheets

(51) Int. Cl.
| | | |
|---|---|---|
| *A61K 8/34* | (2006.01) | |
| *A61K 8/42* | (2006.01) | |
| *A61K 8/73* | (2006.01) | |
| *A61K 8/9789* | (2017.01) | |
| *A61Q 3/00* | (2006.01) | |
| *A61Q 11/00* | (2006.01) | |
| *A61Q 19/00* | (2006.01) | |

(52) U.S. Cl.
CPC ............ *A61K 8/735* (2013.01); *A61K 8/9789* (2017.08); *A61Q 3/00* (2013.01); *A61Q 11/00* (2013.01); *A61Q 19/00* (2013.01); *A61K 2800/87* (2013.01)

(58) Field of Classification Search
CPC ........ A61K 8/345; A61K 8/14; A61K 8/9794; A61K 8/42; A61K 8/0212; A61K 8/38; A61K 8/22; A61K 2800/87
See application file for complete search history.

(56) References Cited

U.S. PATENT DOCUMENTS

| | | | |
|---|---|---|---|
| 9,675,639 B2 | 6/2017 | Shanler et al. | |
| 2002/0054918 A1* | 5/2002 | Murad | A61K 33/40 514/474 |
| 2008/0025926 A1 | 1/2008 | Kavouklis et al. | |
| 2010/0098645 A1 | 4/2010 | Barrett et al. | |
| 2011/0301572 A1 | 12/2011 | Vlodaver et al. | |
| 2014/0154193 A1 | 6/2014 | Barrett et al. | |
| 2014/0213990 A1* | 7/2014 | Gorinshteyn | A61K 31/4166 424/726 |

FOREIGN PATENT DOCUMENTS

| | | | |
|---|---|---|---|
| EP | 2018839 A1 | | 1/2009 |
| EP | 2018839 B1 | | 1/2009 |
| WO | WO 98/34585 | * | 8/1998 |
| WO | 99/20226 A1 | | 4/1999 |
| WO | 02/09653 A1 | | 2/2002 |
| WO | 2004/064881 A1 | | 8/2004 |
| WO | WO 2005/000324 | * | 1/2005 |
| WO | 2006/068857 A1 | | 6/2006 |
| WO | WO 2008/079898 | * | 7/2008 |
| WO | 2011/038446 A1 | | 4/2011 |
| WO | 2012/046229 A2 | | 4/2012 |
| WO | 2016/167498 A1 | | 10/2016 |
| WO | 2017/051293 A1 | | 3/2017 |

OTHER PUBLICATIONS

Enikam Solvenia, "Oxilver® Skin Spray 100ML" and "Oxilver® Skin Gel 30 ML", www.oxilver.com, available in the Internet Archive digital library Sep. 25, 2018 (Sep. 25, 2018), accessed on Nov. 17, 2021 at https://web.archive.org/web/20201031140618/http://www.oxilver.com/.
Oxilver International photograph and comment Published Dec. 9, 2016 (Dec. 9, 2016) of Facebook; accessed on Nov. 18, 2021 https://www.facebook.com/enikam.si/photos/1757443944503794.
Oxilver International photograph and comment Published Nov. 14, 2017 (Nov. 14, 2017) of Facebook; accessed on Nov. 18, 2021 https://www.facebook.com/enikam.si/photos/1895957750652412.
Oxilver International photograph and comment Published Oct. 11, 2017 (Oct. 11, 2017) of Facebook; accessed on Nov. 18, 2021 https://www.facebook.com/enikam.si/photos/1883727811875406.
EPO Communication Pursuant to Article 947(3) EPC; Jan. 25, 2022.
EPO Form 2906; Annex to EPO Communication; Jan. 25, 2022.
Database GNPD [Online] Mintel; Jul. 31, 2018 (Jul. 31, 2018), anonymous: "Anti Tan Facial Kit", XP055689123, retrieved from www.gnpd.com; Database accession No. 5858903.

* cited by examiner

FORMULATIONS CONTAINING ACTIVE OXYGEN COMPOUNDS AND DEVICES FOR APPLICATION THEREOF

FIELD OF THE INVENTION

The present invention relates to formulations with active oxygen compounds that include active oxygen and other active ingredients and adjuvants for the purposes of care for and/or maintaining a healthy condition of skin and of integumentary systems on a surface of a body of an organism and in ears, a healthy condition of nails (fingernail and toenails) and of oral cavity, including its mucous membranes, teeth, interdental spaces and periodontal tissues (gingiva) in the oral cavity, and also to devices or applicators for use of such formulations.

DESCRIPTION OF THE TECHNICAL PROBLEM

The present invention aims to prepare a stable and effective formulation for maintaining a healthy condition of and/or for care for skin, skin structures and integumentary systems on the surface of the body of the organism, including subcutaneous tissues, and in the ears, of nails (fingernail and toenails) and tissues around nails (cuticle), nail structures and systems on the extremities of the body and for maintaining (preserving) the healthy condition of and/or for care for the oral cavity, its mucous membranes, structures and systems, including teeth, interdental spaces and periodontal tissues (gingiva) and structures in the oral cavity.

Namely, on the market we have not found any stable preparations containing active oxygen compounds in compositions, concentrations and combinations with other active ingredients and other ingredients and in forms, as defined by this invention. At the same time, we did not find devices or applicators on the market that included said formulations and preparations for application or use of said formulations that is easy and according to the wishes of the user with defined place or location and time of application of said formulations on the target site of action or target site of the organism.

Therefore, with this invention of the composition and procedures of preparation of such formulations using active oxygen compounds as key active ingredients for maintaining a healthy condition of and/or for care for skin, of finger- and toenails and of oral cavity and related tissues, structures and systems, we are trying to solve also the problem of stability of such formulations and their preparation. At the same time, with this invention we are solving the problem of providing devices or applicators for easy application and according to the wishes of the user with time- and topical-target application or use of said formulations on the target site of action or target site of the organism.

INFORMATION ON THE STATE OF THE ART

Patent application WO 2004/064881 describes a formulation with antibacterial effect in the form of skin treatment ointment, gel or dressing that includes a photocatalytic agent and a substance that acts as an electron donor. When exposed to light in the presence of oxygen, e.g. in ambient air, the photocatalytic agent triggers conversion of oxygen to hydrogen peroxide, which acts in situ (at the site of desired topical action on the skin or in its vicinity) and locally against any bacteria present.

U.S. Pat. No. 9,675,639 discloses stable peroxide formulations and methods and applicators or application devices for their use. The described formulations contain stabilised hydrogen peroxide and 2-propanol, and are used to treat various skin conditions, including warts, Condylomata acuminata or papillomata acuminata (i.e. anogenital warts), seborrhoeic keratosis, mollusca contagiosa or molluscum contagiosum (i.e. benign skin infection) and acrochordons (i.e. benign skin formations).

U.S. Pat. No. 4,826,681 describes a formulation of anhydrous hydrogen peroxide solution in organic solvent for use in therapeutic and cosmetic purposes. The above solution contains from 1 to 20% by weight of hydrogen peroxide and less than 1% by weight of water and is used to treat acne, dermatoses or skin diseases, ulcerations, for skin lightening and/or disinfection of the skin. Cosmetic preparations containing the above solution shall be used, inter alia, for lightening, bleaching and/or oxidative dyeing of hair and/or hair straightening and for similar purposes.

Patent application US 20080025926 discloses formulations for toothpaste, mouthwash (mouth rinse) liquids and gel that include, inter alia, hydrogen peroxide, cetylpyridinium chloride and lycopene. They are intended for oral care and, if necessary, for tooth whitening.

Patent applications US 20100098645 and US 20140154193 describe a formulation and method for the treatment of fungal nail (finger- and toenail) infections caused by the fungi *Trichophyton rubrum* and moulds *Aspergillus niger*. In addition to hydrogen peroxide, the described formulation in the form of an aqueous solution contains also glucose oxidase and D-glucose, whereby the hydrogen peroxide is released in two steps to treat fungal infections of finger- and toenails. Both applications disclose antimicrobial formulation that is stable in terms of storage with pH value ranging from approx. 4 to 8 that in addition to D-glucose also includes other sugars selected from sucrose, fructose and/or maltose. Hydrogen peroxide is released from this formulation in two steps, namely the hydrogen peroxide that is stable in terms of storage is biologically available for immediate release in said formulation at a concentration of at least 10 mg per litre and for slow release during a 24-hour period based on the rehydration of the formulation. Said formulation that penetrates into and through the nail (finger- or toenail) plate has an antifungal and antispore effect.

In the published patent documents we have not found a solution to the technical problem as described here that would solve the said problem by preparation, composition and form of formulations in a manner and in combination of technical characteristics, i.e. in the combination of formulation ingredients and in the form of formulations, as being solved by this invention as described here and defined in patent claims.

Figure 1:
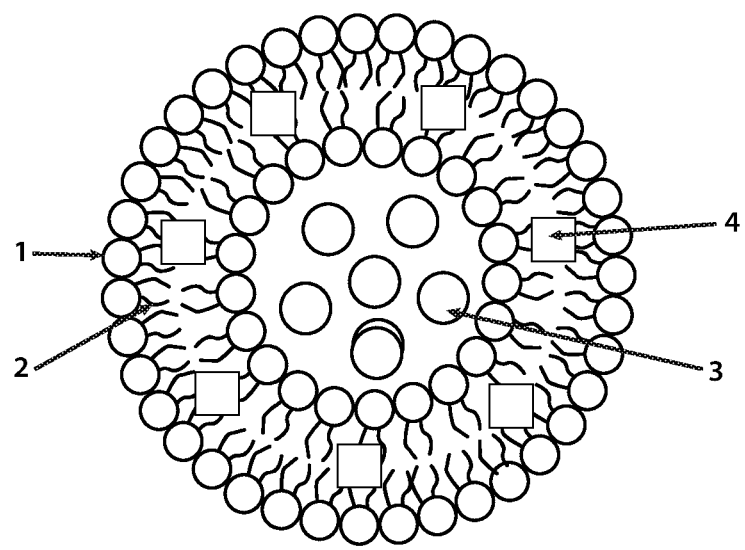
FIG. 1 schematically shows a liposome with the formulation that contains active oxygen compounds according to this invention as one of the implementation examples of the formulation within the meaning of this invention.

The forms of formulations according to this invention and devices or applicators for their application on target sites of the organism within the meaning of the described invention as schematically shown and/or described in this description of the figures and/or in other sections of this description of the invention, represent only some of the possible implementation examples of forms of formulations according to this invention.

DESCRIPTION OF A NEW SOLUTION TO THE TECHNICAL PROBLEM

The present invention solves the technical problem posed by the preparation of a stable formulation that includes stabilised active oxygen compounds as key or main active ingredient which are obtained through a special technological process of production and purification from hydrogen peroxide (chemical formula: $H_2O_2$) and which is used for care for, maintenance and preservation of a healthy condition of the target areas of the organism. The specified target areas of the organism within the meaning of this invention are predominantly the skin, nails (finger- and toenails) and/or oral cavity and related tissues, mucous membranes (mucosa), structures and systems, as known in the state of the art.

The subject matter of this invention are different types and forms of formulations according to the composition or formulation ingredients and physical form of formulations, such as for example solution, mouthwash (mouth rinse), spray, gel, paste, emulsion, lotion, milk and/or cream and various forms of formulations with controlled release of formulations agents and ingredients, as they are selected from among the controlled release formulations as known and used in the state of the art, and among which are preferably liposomes, mycelia and film dressings.

Furthermore, the subject matter of this invention are formulations according to this invention that are included in or incorporated into the applicators or devices for the application of this formulation on and/or into the target area of the organism, among which are patches, dental showers, toothbrushes and interdental toothbrushes.

The formulations according to this invention include stabilised active oxygen compounds as the key or main active ingredient or active agent and, in addition to these, silver in an ionised and colloidal form and/or gold in an ionised and colloidal form as a second key active ingredient or active agent in formulations, as well as other ingredients that are called passive components or ingredients of the formulation within the meaning of this invention and the remaining components as supplemental ingredients of the formulation.

Passive ingredients and supplemental ingredients moderate the composition of formulations according to this invention with the aim to amplify the effects of formulations with a view to providing care for, maintaining and preserving a healthy condition of skin, subcutaneous tissues and nails (finger- and toenails) as well as providing a healthy condition of their tissues, mucous membranes, structures and systems and/or with a view to providing care for, maintaining and preserving a healthy condition of the oral cavity, including the teeth and periodontal tissues (gingiva) and a healthy condition of the tissues, mucous membranes, systems and structures of the oral cavity and teeth.

The formulation for the care for, maintenance and preservation of a healthy condition of skin, subcutaneous tissues and finger- and toenails and their tissues, mucous membranes, structures and systems within the meaning of this invention is in the form of a solution, spray, gel, emulsion, lotion, milk, cream, film dressings, liposomes and/or mycelia and, if necessary, it is included in the application patches for application of this formulation to and/or into the target area of the organism.

The formulation for the care for, maintenance and preservation of a healthy condition of the oral cavity and/or tissues, mucous membranes, systems and structures of the oral cavity, including teeth, periodontal tissues and interdental spaces is in the form of a solution, mouthwash, spray, gel, paste and/or emulsion and/or in the form of controlled release formulations, which predominantly include film dressings, liposomes and/or mycelia and, if necessary, it is included in patches, dental showers, toothbrushes and/or interdental brushes for application of this formulation to and/or into the target area of the organism. In addition to the preferred formulations with controlled-release of active ingredients, there are other similar formulations within the meaning of this invention, as known in the existing state of the art to enable controlled release of active ingredients.

The target areas of the organism, on which the formulation with active oxygen compounds are administered according to this invention, are any areas of the organism on which the formulation is active in such a way that the formulation provides care for and/or maintains them and/or preserves a healthy condition of such areas of the organism. Preferably, such areas of the organism include skin, subcutaneous tissues and nails (finger- and toenails) and tissues, mucous membranes (mucosa), tissue structures and systems consisting of skin, subcutaneous tissues and finger- and toenails and the oral cavity and/or tissues, mucous membranes (mucosa), systems and structures of the oral cavity, including teeth, periodontal tissues (gingiva) and interdental spaces as they are known in the state of the art. Most preferably such areas of the organism include target tissues, mucous membranes (mucosa), structures and systems of the organism.

The organism within the meaning of this invention is preferably a human organism. In alternative implementations (embodiments) of the invention, the organism may also be an animal organism and preferably an animal organism with tissues, mucous membranes, structures and systems within the meaning of this invention.

Controlled release of active ingredients or active agents within the meaning of this invention means the release of the active ingredients, as defined in this invention, at a specific site of target areas of the organism and/or target tissues, mucous membranes, structures and systems of the organism and at the same time release occurring at a specified time or time interval and/or according to a specific time pattern.

Release occurring at a specified time or time interval within the meaning of this invention means release of the active ingredients precisely at the time desired by the user of the formulation, which is performed in the case of the formulation according to this invention incorporated in the dental shower, toothbrush and/or interdental toothbrush. The release of the formulation is controlled by the user by pushing the brush push-button, which enables the inflow and/or application of the said formulation directly to the location of the brush placement through the brush nozzles as described in the implementation examples (examples of embodiments).

A particular time pattern of active ingredient release within the meaning of this invention is preferably either the release of the active ingredients when certain conditions are fulfilled or the delayed release of the active ingredients.

Alternative implementations (embodiments) of the invention also provide a time-based release pattern of the active ingredients as well as any other active ingredient release pattern that is selected from patterns as known in the prior art, preferably in the fields of pharmacy, medicine, cosmetics and/or veterinary medicine.

The release of the active ingredients when certain conditions within the meaning of this invention have been fulfilled, is the release of the active ingredients over a time interval when the formulation according to this invention comes into contact with the target areas of the organism and most preferably into contact with the target tissues, mucous membranes, structures and systems of the organism.

The delayed release of the active ingredients within the meaning of this invention is the release of the active ingredients over a time interval when the formulation according to the present invention comes into contact with the target area of the organism and most preferably comes into contact with the target tissues, mucous membranes, structures and systems of the organism, and when, at the same time, such release is regulated by the ingredients of the formulation so that the active ingredients and ingredients are not released immediately, but in a delayed manner. For example, this is enabled by specific forms and ingredients of the formulation as they are known in the state of the art with respect to selected active ingredients in the formulation according to this invention. Preferably, these are formulations in the form of liposomes, mycelia, patches and film dressings. A formulation in the form of liposomes and/or mycelia is the so-called micro-formulation according to this invention that includes a key active ingredient, i.e. the active oxygen compounds in the gel medium or in the medium of gel within the meaning of this invention. Such micro-formulation in the form of liposomes or mycelia is then incorporated into the macro-formulation according this invention, which is a formulation within the meaning of this invention which, with the exception of the active oxygen compounds in the micro-formulation, includes other ingredients of the formulation according to this invention. Alternatively, in the liposomes and mycelia benzoyl peroxide in a weight concentration of from and including 5 wt. % up to and including 20 wt. % of benzoyl peroxide or carbamide peroxide in a weight concentration of from and including 5% by weight up to and including 20 wt. % of carbamide peroxide may be included as the main or key active ingredient of the formulation instead of hydrogen peroxide in weight concentration with respect to the entire formulation (hereinafter also referred as: % by weight) from and including 1% by weight up to and including 6 wt. % of hydrogen peroxide. For faster release of active oxygen compounds, a peroxidase enzyme may be present in the liposome envelope or membrane, if necessary, such as is shown FIG. 1.

In these formulations, the delayed release of the active ingredients regulates the contact of the patches contact surface, film dressings, liposome and/or mycelium with the target site of functioning, i.e. with the target area of the organism and passage and/or diffusing of the formulation and its active ingredients and components on and/or into the target area of the organism, preferably under the influence of substances such as components of exudate and due to elements such as ambient temperature at or in the target area of the organism.

The film dressings according to this invention that is originally in the form of a cream, paste, gel and/or other formulation of similar type according to this invention is applied to the desired site of functioning, i.e. the target site of the organism and hardens in contact with it so that it forms the dressing or coating and acts on it at a specified time interval ranging from 2 minutes to 5 hours, and preferably from 5 minutes to 3 hours, more preferably 30 minutes and most preferably from 5 minutes to 15 minutes. During this time, the active ingredients and ingredients from the dressing or coating pass through and/or diffuse on and/or into the target area of the organism. Ingredients for making creams, paste, gel and/or other similar formulations that enable at the target site of functioning or at the target site of the organism in contact with adjacent elements such as saliva and/or air and micro-ambient temperature, i.e. environment on or in the target part of the organism, the formation of a film dressing at the target area of the organism and thereby the holder part of the film dressing, are selected from ingredients as they are known and used in the state of the art in the field of pharmacy and/or medicine and as they are described herein in the implementation example of formulation in the gel form. Also included in the holder part is a formulation within the meaning of this invention. When the applied gel, paste, cream and/or other similar formulations contact the adjacent elements, a flexible film-like layer is formed on the outside of the dressing that is most preferably waterproof and/or hydrophobic, while on the inner side the dressing is in contact with the site of functioning or the target area of the organism in such a way as to allow the passage and diffusion of the active ingredients and ingredients on and/or into the target area of the organism and is preferably hydrophilic. This target area of the organism is in the oral cavity, e.g. site of inflammation, oral ulcers, injuries and/or tissue wounds. Similarly, this target area on the skin, nails (finger- and toenails) and/or cuticle tissues is, for example, the site of inflammation, site of infection, site of injury and/or wound on the skin, finger- and toenail and/or cuticle tissue or tissues thereof, mucous membranes, structures and systems.

According to this invention, the patch consists of a holder, a pad or matrix attached to it containing the formulation according to this invention including the formulation in the form of liposomes and/or mycelia for the purpose of delayed release of the active ingredient that consists of active oxygen compounds.

Figure 5:
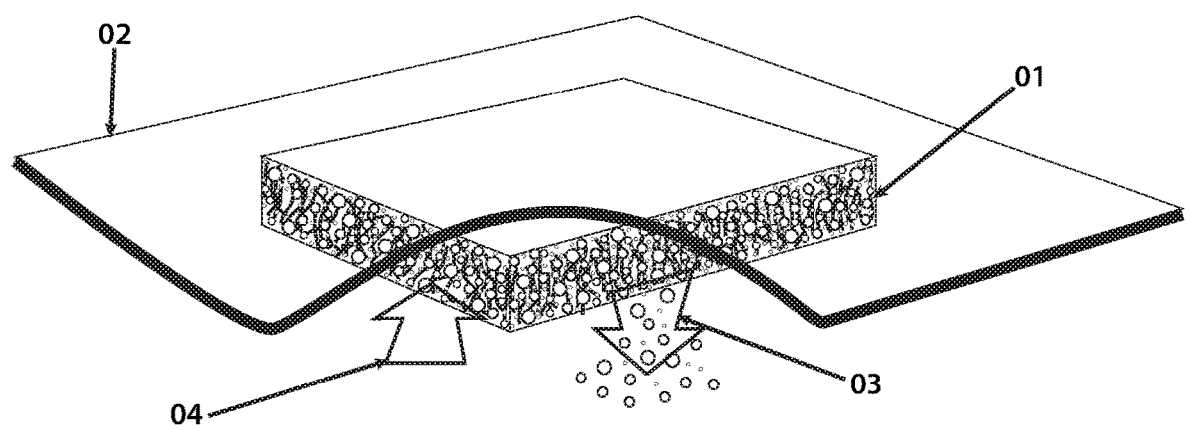
FIG. 5 schematically shows one of the implementation examples of the patch with the formulation according to this invention for use on skin and integumentary systems where the active oxygen compounds that are contained in the liposomes of the gel medium and which are, together with other ingredients of the formulation, embedded in the pad or matrix of the patch, are released in a controlled manner over a certain time period. In addition, the figure shows a ¾ view of the patch with removed front angled part of the patch for the purpose of more thorough presentation of the patch pad and of the movement direction of the formulation ingredients from the patch pad and of the direction of movement of ambient substances (exudate) into the patch pad or of functioning of ambient elements (temperature) at the target site of the organism on the patch pad.

The pad or the matrix is preferably attached in the middle area of the patch, i.e. on the self-adhesive part attached to it at the outer edges of the patch, which is slightly away from and surrounding the pad. The patch, its holder, the pad and the self-adhesive part can be of any shape and size. These shapes and sizes depend on the target area of the organism to which the patch is being applied. Preferably, according to this invention, the patch is of any rectangular, square, circular, elliptical, triangular, trapezoidal and/or other similar shape and with one diameter ranging from 0.5 cm to 20 cm and at the same time with another diameter ranging from 0.5 cm to 15 cm. More preferably, according to this invention, the patch is with one diameter ranging from 1 cm to 10 cm and at the same time with another diameter ranging from 1 cm to 5 cm. Even more preferably, according to this invention, the patch is with one diameter ranging from 1 cm to 8 cm and at the same time with another diameter ranging from 1 cm to 3 cm. When it is circular in form, according to this invention, the patch is 5 cm in diameter, preferably 4 cm in diameter and most preferably 3 cm in diameter. For use in the oral cavity, the diameter of the circular patch preferably ranges from 1 cm to 2.5 cm and most preferably within the range from 1.5 cm to 2 cm. The patch and its components that include the patch holder, pad and self-adhesive part, are made of materials as known and used in the state of the art in the field of pharmacy for production of patches and their components. Preferably, the patch holder is made of polymeric natural and/or artificial materials, the pad or matrix are also made of polymeric natural and/or artificial materials, and the self-adhesive part applied to the holder at the edges of the patch, is made of adhesive silicone and/or other similar, preferably polymeric materials that are adhesive to skin and mucous membranes. An example of a patch according to this invention is shown in FIG. 5.

The formulation in the form of liposomes and/or mycelia according to this invention allows the controlled release of active oxygen compounds. Liposomes such as shown in schematic FIG. 1 of the liposome structure, and mycelia such as shown in schematic FIG. 3 of the mycelium structure have in their core surrounded by a phospholipid envelope or membrane a micro-formulation according to this invention with active oxygen compounds in the gel medium according to this invention, i.e. a formulation comprising as a source of active oxygen compounds a hydrogen peroxide molecule in a weight concentration of the entire formulation of from and including 1 wt. % to 6 wt. % of hydrogen peroxide in the entire formulation or alternatively benzoyl peroxide molecules in a weight concentration of the entire formulation of from and including 5 wt. % to 20 wt. % of benzoyl peroxide or further alternatively carbamide peroxide molecules in a weight concentration of the entire formulation of from and including 5 wt. % to 20 wt. % of carbamide peroxide. The gel medium in the micro-formulation according to this invention, which is the adjacent medium of the active oxygen compounds in the micro-formulation consists of the ingredients according to this invention, among which there are preferably the hyaluronic acid, panthenol, and various active ingredients of plant origin, which are selected from active ingredients of plant origin, as they are known and used in the state of the art in the fields of cosmetics, pharmacy and food industry. These various active ingredients are preferably of natural and plant origins. Most preferably these include the active ingredients of ginger (*Zingiber officinale*), purple cornflower (*Echinacea purpurea*), myrrh (*Commiphora abyssinica*), marigold (*Calendula officinalis*), and/or St. John's wort (*Hypericum perforatum*), and other plants that are according to the state of the art in the cosmetics, pharmacy and/or food industry used as active ingredients of plant origin. Most preferably these are extracts from said plants and/or parts thereof. It is extremely preferable that such active ingredients of plant origin are selected from a combination of these, which are industrially or otherwise prepared, such as e.g. plant extracts or parts thereof. These are marketed under different names depending on the manufacturer and depending on the active ingredients have different effects on the target tissues, mucous membranes, structures and/or systems. For example, they are selected from among the products of the company Symrise AG under the trade name Actipone® that includes ginger (*Zingiber officinale*; namely an extract of its root), active ingredients of purple cornflower (*Echinacea purpurea*, namely its extract) and active ingredients of myrrh or myrtle (*Commiphora abyssinica*, namely an extract of its resin), which in addition to these active ingredients also contain, inter alia, water, glycerine or glycerol, polysorbate, preservatives, sodium benzoate and/or potassium sorbate, and is for anti-irritant or soothing effect recommended for use in a concentration of 0.02 wt. % to 0.65 wt. % of the formulation, for antioxidative effect in a concentration of 1.25 wt. % and for antimicrobial effect in a concentration of 1.05% by weight to 4.20 wt. %.

According to this invention, the liposome and/or mycelium macro-formulation that is preferably in the form of a gel, emulsion and/or cream, there are also other ingredients of the formulation within the meaning of this invention, i.e. others or i.e. other key active ingredients such as silver and/or gold in ionised and colloidal form and other ingredients, i.e. passive ingredients of the formulation and the remaining or supplemental ingredients of the formulation as defined in hereby description of the invention.

According to this invention, the liposomes are preferably spherical in shape and are two- or multi-layered, or have a two- or multi-layered envelope or membrane surrounding the liposome core. According to this invention, the mycelia are preferably spherical in shape and monolayered or have a single-layer envelope or membrane surrounding the mycelium core.

The envelope consists of phospholipid molecules. Each phospholipid molecule has a polar part or the so-called polar head 1 that has hydrophilic properties, and a two-pointed lipophilic or hydrophobic part or the so-called hydrophobic tail 2. The phospholipid molecules are structured and oriented in the liposome membrane in such a way that one membrane lamella is arranged on the outside of the liposome so that the polar heads of the liposomes are arranged sequentially on its outer side, while the hydrophobic tails of the phospholipids that are oriented towards the liposome membrane's core, are on its inner side. The second membrane lamella of the liposome or the inner layer has polar heads that are sequentially arranged on the inside of the liposome, i.e. at the nucleus or liposome core, and hydrophobic tail of phospholipids oriented towards the liposome membrane core. Thus, the liposome has a hydrophilic layer or hydrophilic microenvironment on the outside of the liposome as well as by the nucleus/core of the liposome and the hydrophobic layer or hydrophobic microenvironment within the liposome membrane or in the so-called liposome membrane core.

Figure 3:
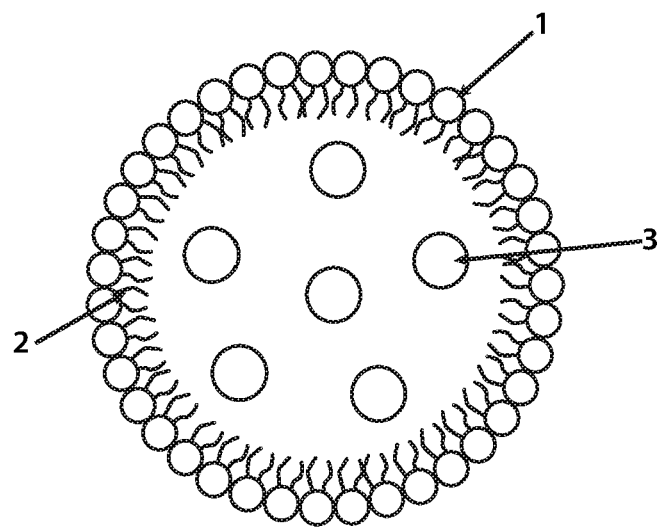
FIG. 3 schematically shows a mycelium with a formulation that contains active oxygen compounds according to this invention as one of the implementation examples of the formulation within the meaning of this invention.
Figure 4:
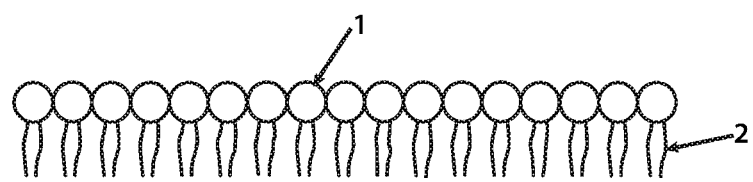
FIG. 4 schematically shows a single-layer phospholipid mycelium envelope structure as shown in FIG. 3.

One layer or a single-layer mycelium envelope that is e.g. schematically shown in FIG. 4 consists of a series of sequentially stringed phospholipid molecules, oriented in space so that on one side there are hydrophilic heads 1 of phospholipid molecules that contact each other and on the other side hydrophobic tails 2 of these molecules, as is schematically shown in FIGS. 3 and 4. Therefore, there is a hydrophilic microenvironment at the heads of phospholipids 1 and a hydrophobic microenvironment at their tails 2.

Figure 2:
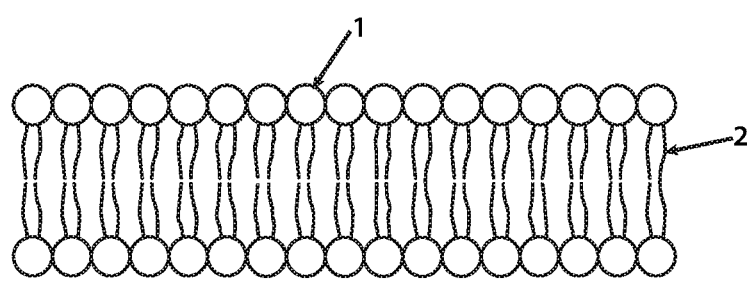
FIG. 2 schematically shows a two-layer phospholipid membrane or liposome envelope structure as shown in FIG. 1.

A double layer or a double-layer liposome envelope or membrane that is e.g. schematically shown in FIG. 2 consists of an inner and outside series of sequentially stringed phospholipid molecules, oriented in space so that on one side there are hydrophilic heads 1 of phospholipid molecules that contact each other and on the other side hydrophobic tails 2 of these molecules, as is schematically shown in FIGS. 1 and 2. Therefore, there is a hydrophilic microenvironment at the heads of phospholipids 1 and a hydrophobic microenvironment at their tails 2. Therefore, in the double-layer liposome envelope, as shown in FIG. 1, the hydrophilic environment is at the core of the liposome and on the outside around the liposome, while the hydrophobic environment in the inner layer of the film is between the contacting hydrophobic tails of the phospholipids. In alternative implementations of this invention, the peroxidase enzyme 4 is also included in the hydrophobic environment of the double-layer liposome envelope, as shown in FIG. 1.

The peroxidase enzymes according to this invention are selected from peroxidase enzymes, including myeloperoxidase, lactoperoxidase, horseradish peroxidase and other peroxidases as known in the state of the art. They regulate the rate of release of active oxygen compounds that is accelerated in the presence of these enzymes. The basic implementation example includes an enzyme-free liposomal formulation.

In the mycelium core, as e.g. in FIG. 3, or in the liposome core, as e.g. in FIG. 1, there is according to this invention the key active ingredient, i.e. active oxygen compounds in the gel medium 3 according to this invention, the source of which is preferably hydrogen peroxide according to this invention and alternatively benzoyl peroxide or carbamide peroxide.

Such a formulation can be used in the oral cavity or on the skin, including their tissues, mucous membranes, structures and systems. Liposome with its structure that has a double layer or two-lamellar or multi-lamellar envelope, or mycelium with its single-layer film structure, allow the controlled release of active oxygen compounds. For example, in the oral cavity, this is achieved with the effect of the ambient temperature in the oral cavity and saliva on liposomes, while on the skin this occurs through the effect of the ambient temperature and exudate on the skin.

The subject matter of the invention described herein is a formulation with active oxygen compounds for the maintenance and preservation of a healthy condition of and/or for care for the skin, its tissues, mucous membranes, structures and systems, including subcutaneous tissues, nails (finger- and toenails) and cuticle tissues, and for maintenance and preservation of a healthy condition of and/or for care for the oral cavity, its tissues, mucous membranes, structures and systems, including teeth, periodontal tissues, interdental spaces and their structures and systems that contains the following:

hydrogen peroxide as a key active ingredient and source of active oxygen compounds in the formulation;

silver in ionised and colloidal form and/or gold in ionised and colloidal form, another key active ingredient in a formulation with the function of a mild antiseptic agent;

aloe vera as a passive ingredient or component in the formulation with a skin care function;

hyaluronic acid or its sodium salt, sodium hyaluronate as a passive ingredient or component in a formulation with the function of a moisturiser or humectant and with skin care function;

if necessary, additional moisturiser, as a passive ingredient or a component in a formulation with the function of a moisturiser or humectant and, if necessary, skin care function, and/or if necessary, panthenol, and/or if necessary, one or more flavourings, and/or if necessary, one or more perfumes, and/or if necessary, gelling agent for certain forms of formulations;

if necessary, other supplemental ingredients including various oils, various vitamins, fatty acids, minerals, various active ingredients of plant origin, antioxidants and/or other similar ingredients, and/or if necessary, glycerine or glycerol.

Preferably, this is a formulation with active oxygen compounds for the maintenance and preservation of a healthy condition of and/or for care for the skin, its tissues, mucous membranes, structures and systems, including subcutaneous tissues, nails (finger- and toenails) and cuticle tissues, and for maintenance and preservation of a healthy condition of and/or for care for the oral cavity, its tissues, mucous membranes, structures and systems, including teeth, periodontal tissues, interdental spaces and their structures and systems that contains hydrogen peroxide and also includes the following:

silver in colloidal form and/or gold in colloidal form;

aloe vera;

hyaluronic acid and/or additional moisturiser.

According to this invention, the formulation also includes panthenol, if necessary.

In an alternative implementation example and/or if necessary, the formulation according to this invention the formulation includes one or more flavours and/or one or more perfumes.

In a further alternative implementation example, the formulation according to this invention further or if necessary, also includes a gelling agent.

In addition to the above ingredients, the formulation according to this invention in further implementation examples or if necessary, also includes supplemental ingredients that are preferably selected from various oils, vitamins, fatty acids, minerals, active ingredients of plant origin and/or antioxidants.

In an alternative implementation example and/or if necessary, the formulation according to this invention also includes glycerine or glycerol and/or hyaluronic acid.

In the formulation with the active oxygen compounds according to this invention, hydrogen peroxide is present in a weight concentration ranging from and including 0.5 weight shares or percentages or % up to and including 6 weight % of the formulation (hereinafter referred to as parts or percentages by weight or % by weight of the total weight of the formulation, abbreviated as: wt. %). In alternative implementations of the formulation with active oxygen compounds according this invention, hydrogen peroxide is preferably present in a concentration ranging from and including 1.5 wt. % up to and including 3 wt. % of the formulation and most preferably either in a concentration of 1.5 wt. % of the formulation or in a concentration of 3 wt. % of the formulation.

Hydrogen peroxide and active oxygen compounds released from it are a key active ingredient or active agent of the formulations according to this invention and have a mild antiseptic effect and help regenerate the skin. They have an antimicrobial effect against pathogens that, inter alia, include bacteria, viruses and fungi, and thus help prevent infections.

Hydrogen peroxide for formulations according to this invention is obtained through a technological process for production and purification of anthraquinone-derived hydrogen peroxide, as it is known in the state of the art in the field of chemistry. Any organic and inorganic substances that are present as a residue from the chemical processes used in deriving hydrogen peroxide through the anthraquinone process are removed from the hydrogen peroxide thus obtained. For these purposes, hydrogen peroxide is further purified through a membrane filtration process, mainly to achieve its high purity for use for cosmetic and/or nutritional purposes (namely, for nutritional use or food grade use) and, if necessary, also for pharmaceutical purposes, as required by the currently valid European Pharmacopoeia 8th Edition, abbreviation: Ph. Eur. 8th. At the same time, this hydrogen peroxide is stabilised by stabilisers selected from stabilisers that include sodium pyrophosphates, colloidal stannates, organophosphonates, nitrates and phosphoric acid, and, if necessary, also colloidal silicates and other similar stabilisers authorised for nutritional purposes or nutritional use or food grade use and safe for ingestion in formulations with either food and/or medicinal products. Hydrogen peroxide is preferably stabilised with sodium pyrophosphates, most preferably the stabiliser is disodium dihydrogen pyrophosphate (chemical formula: $Na_2H_2P_2O_7$), whereby the phosphate ion concentration does not exceed 0.005 wt. %.

Silver in ionised and colloidal form and/or gold in ionised and colloidal form in the formulation is present at a concentration of from and including 0.1 wt. % up to and including 4 wt. % of the formulation. Silver in ionised or ionic and colloidal form used alone is present in a weight concentration within a range of from and including 0.1 wt. % up to and including 4 wt. % of the formulation. Gold in ionised or ionic and colloidal form used alone is present in a concentration within a range of from and including 0.1 wt. % up to and including 4 wt. % of the formulation. When both silver and gold are present in the formulation simultaneously, then their total share amounts from and including 0.1 wt. % up to and including 4 wt. % of the formulation. Preferably, such silver or gold when present in the formulation alone or when both are present simultaneously, is present in the concentration of a single ingredient or in a total concentration of both ingredients, either 0.1 wt. %, 0.5 wt. %, 1 wt. %, 1.5 wt. %, 2 wt. %, 2.5 wt. %, 3 wt. %, 3.5 wt. % or 4 wt. of the formulation.

The above stated silver or gold in the formulation according to this invention acts as the second key active ingredient in addition to hydrogen peroxide and has the primary function of a mild antiseptic agent. Silver (Ag) that is in ionic or ionised and colloidal form and/or gold (Au) that is in ionic and colloidal form has a mild antiseptic effect and in addition helps stabilise formulations that include hydrogen peroxide. The silver (Ag) within the meaning of this invention is selected from the colloidal ionic forms of silver and as they are used in the state of the art in the field of food industry, pharmaceutical and cosmetic fields. The gold (Au) within the meaning of this invention is selected from the colloidal ionic forms of gold and as they are used in the state of the art in the field of food industry, pharmaceutical and cosmetic fields.

In the formulations according to this invention, aloe vera is present in a weight concentration within a range of from and including 0.2 wt. % to up to and including 10 wt. % of the formulation and preferably in a concentration of either 0.2 wt. %, 0.3 wt. %, 0.4 wt. %, 0.5 wt. %, 1 wt. %, 1.5 wt. %, 2 wt. %, 2.5 wt. %, 3 wt. %, 3.5 wt. %, 4 wt. %, 4.5 wt. %, 5 wt. %, 5.5 wt. %, 6 wt. %, 6.5 wt. %, 7 wt. %, 7.5 wt. %, 8 wt. %, 8.5 wt. %, 9 wt. %, 9.5 wt. % or 10 wt. % of the formulation.

According to this invention, aloe vera is selected from substances derived from different species of aloe vera that have been selected from *Aloe barbadensis*, *Aloe arborescens* and/or *Aloe ferox*, all of which are of the Liliaceae family. Preferably, it is a herbal substance derived from the leaves of the species *Aloe barbadensis*. It acts on the skin as a skin softener. Alternatively, it is an extract of leaves of the *Aloe* species *Aloe barbadensis*, an extract of aloe flowers of the species *Aloe barbadensis* or a gel that is extruded from the leaves of the species *Aloe barbadensis*, whereby all of these substances act as a skin softener. In other alternative implementations of the invention, aloe vera is an *Aloe arborescens* leaf extract or an *Aloe ferox* leaf extract, whereby both these extracts act as a moisturiser and as a soothing agent for the skin, mucous membranes and related structures and systems. Aloe vera in the formulation according to this invention represents a passive ingredient or component in a formulation with skin care function.

The moisturiser is present in a weight concentration within a range of from and including 0.2 wt. % up to and including 10 wt. % of the formulation. Preferably, the moisturiser is present in a concentration of either 0.2 wt. %, 0.3 wt. %, 0.4 wt. %, 0.5 wt. %, 1 wt. %, 1.5 wt. %, 2 wt. %, 2.5 wt. %, 3 wt. %, 3.5 wt. %, 4 wt. %, 4.5 wt. %, 5 wt. %, 5.5 wt. %, 6 wt. %, 6.5 wt. %, 7 wt. %, 7.5 wt. %, 8 wt. %, 8.5 wt. %, 9 wt. %, 9.5 wt. % or 10 wt. % of the formulation.

Hyaluronic acid or its sodium salt, sodium hyaluronate, is present in the formulation according to this invention in a weight concentration within a range of from and including 0.2 wt. % up to and including 10 wt. % of the formulation. Preferably, the hyaluronic acid is present in a concentration of either 0.2 wt. %, 0.3 wt. %, 0.4 wt. %, 0.5 wt. %, 1 wt. %, 1.5 wt. %, 2 wt. %, 2.5 wt. %, 3 wt. %, 3.5 wt. %, 4 wt. %, 4.5 wt. %, 5 wt. %, 5.5 wt. %, 6 wt. %, 6.5 wt. %, 7 wt. %, 7.5 wt. %, 8 wt. %, 8.5 wt. %, 9 wt. %, 9.5 wt. % or 10 wt. % of the formulation.

Hyaluronic acid or its sodium salt, sodium hyaluronate, is a passive ingredient or component in the formulation according to the present invention. It has the function of a moisturiser or humectant and a skin care function. The sodium hyaluronate within the meaning of this invention is the sodium salt of hyaluronic acid. When using the formulation according to this invention on the target tissues or mucous membranes, systems and structures as they are defined within the meaning of this invention, it has a dual function, namely it penetrates into the target tissue or mucous membrane and/or forms a thin film on its surface that prevents excessive loss of water from the target tissue/mucous membrane. In this way it contributes to the retention of moisture in the target tissue/mucous membrane, while at the same time reduces the evaporation of water from the tissue/mucous membrane with a thin film and protects against environmental elements and factors (wind, cold, dust, various chemicals), thereby contributing to the moisturising of the tissue/mucous membrane and indirectly to the elasticity of the tissue/mucous membrane and to the accelerated healing of any injuries and/or wounds on the tissue/mucous membrane.

As a moisturising agent or humectant within the meaning of this invention, in addition to hyaluronic acid or sodium hyaluronate any other moisturiser is also selected from the moisturisers as they are known and used in the state of the art in the fields of cosmetics and/or cosmetic, food and/or pharmaceutical industries. Preferably, in addition to hyaluronic acid or sodium hyaluronate, glycerine or glycerol, which act as a moisturiser or humectant, are also used as moisturisers. The humectant binds water and thus enables preservation of the proper level of humidity of the formulation.

When the formulation includes a combination of moisturisers or humectants, then their total share in the formulation lies within a range of from and including 0.2 wt. % up to and including 10 wt. % of the formulation. Such formulations preferably have, in addition to hyaluronic acid, the above additional moisturiser so that the total concentration of hyaluronic acid and additional moisturiser in the formulation is within a range of from and including 0.2 weight % up to and including 10 weight % of the formulation.

Furthermore, in this formulation if necessary and/or in variant implementations, panthenol is also present in a weight concentration within the range of from and including 0.2 wt. % to up to and including 10 wt. % of the formulation and preferably in a concentration of either 0.2 wt. %, 0.3 wt. %, 0.4 wt. %, 0.5 wt. %, 1 wt. %, 1.5 wt. %, 2 wt. %, 2.5 wt. %, 3 wt. %, 3.5 wt. %, 4 wt. %, 4.5 wt. %, 5 wt. %, 5.5 wt. %, 6 wt. %, 6.5 wt. %, 7 wt. %, 7.5 wt. %, 8 wt. %, 8.5 wt. %, 9 wt. %, 9.5 wt. % or 10 wt. % of the formulation. Panthenol is dexpanthenol and has the chemical formula 2,4-dihydroxy-N-(3-hydroxypropyl)-3,3-dimethyl-, (2R)-butanamide. It acts as a skin care agent and as an antistatic agent.

The flavour is present in the formulation according to this invention if necessary and/or in variant implementations of the formulations, namely it is present in a weight concentration within a range of from and including 0.01 wt. % up to and including 1 wt. % of the formulation and preferably at a concentration of either 0.01 wt. %, 0.02 wt. %, 0.03 wt. %, 0.04 wt. %, 0.05 wt. %, 0.06 wt. %, 2 wt. %, 0.07 wt. %, 0.08 wt. %, 0.09 wt. %, 0.1 wt. %, 0.15 wt. %, 0.20 wt. %, 0.25 wt. %, 0.3 wt. %, 0.35 wt. %, 0.4 wt. %, 0.45 wt. %, 0.5 wt. %, 0.6 wt. %, 0.65 wt. %, 0.7 wt. %, 0.75 wt. %, 0.8 wt. %, 0.85 wt. %, 0.9 wt. %, 0.95 wt. % or 1 wt. % of the formulation.

The flavour within the meaning of this invention is selected from those used in the prior art in the fields of cosmetics, pharmaceutical and/or food industries. Preferably, the flavour is selected from flavours that include the flavour of tangerine, lemon and peach. In variant implementations of the formulation according to this invention, the flavour also includes any of the flavours that include flavours of lemon grass, blueberry, strawberry, currant, blackberry, raspberry, cherry, sour cherry, apple, pear, banana, plum, vanilla, cinnamon, ginger (*Zingiber officinale*), purple cornflower (*Echinacea purpurea*), cloves, rosemary, rum, cocoa, jasmine, mint, menthol, spearmint, stevia, myrrh (*Commiphora abyssinica*) and other flavours that are used as flavours in the state of the art in the field of cosmetics, pharmaceutical and/or food industries. The flavours within the meaning of this invention include natural and/or synthetic flavours. In case of natural flavours, the extracts are from said plants and/or parts thereof. The flavour in the formulation has the function of formulating or moderating the taste of the formulation according to this invention. According to this invention, one flavour as well as more flavours can be included in the formulation at the same time.

The fragrance or perfume is present if necessary and/or in variant implementations of the formulations according to this invention. It is present in a weight concentration within a range of from and including 0.01 weight % up to and including 3 weight % of the formulation. When the formulation includes a combination of fragrances or perfumes, then their total share in the formulation lies within a range of from and including 0.01 weight % up to and including 3 weight % of the formulation. Preferably, said concentration of one and/or more perfumes is either 0.02 wt. %, 0.03 wt. %, 0.04 wt. %, 0.05 wt. %, 0.06 wt. %, 0.07 wt. %, 0.08 wt. %, 0.09 wt. %, 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.2 wt. %, 1.3 wt. %, 1.5 wt. %, 1.7 wt. %, 1.8 wt. %, 2 wt. %, 2.1 wt. %, 2.2 wt. %, 2.3 wt. %, 2.4 wt. %, 2.5 wt. %, 2.6 wt. %, 2.7 wt. %, 2.8 wt. %, 2.9 wt. % or 3 wt. % of the formulation.

The fragrance or perfume is selected from perfumes that are and as they are used in the state of the art in the field of cosmetics, pharmaceutical and/or food industries. Preferably, it is selected from perfumes that include perfumes of lemons, limes, oranges, tangerines, bergamot oranges, roses, violets, rosemary, laurel, thyme, sage, juniper berries, honey, jasmine, lavender, pine, spruce, birch, lilac, wild chestnut and/or myrrh (*Commiphora abyssinica*). Perfumes or fragrances within the meaning of this invention are synthetic and/or natural, preferably these are synthetic fragrances. In case of natural fragrances, the extracts are from said plants and/or parts thereof. The function of fragrance or perfume in the formulation is to formulate or moderate the odour of the formulation according to this invention. The formulation according to this invention may contain one fragrance or one perfume, as well as more than one fragrance or perfume at the same time.

The gelling agent is an ingredient of the formulations according to this invention that is present in variant implementations of the formulations and/or if necessary. Preferably, the gelling agent is present in formulations in the form of gel, film dressing and/or emulsion and, if necessary, in formulations in the form of creams and lotions as well. The gelling agent is present in the formulations in a weight concentration within a range of from and including 1 wt. % up to and including 30 wt. % of the formulation and preferably in a concentration of either 1 wt. %, 2 wt. %, 3 wt. %, 4 wt. %, 5 wt. %, 6 wt. %, 7 wt. %, 8 wt. %, 9 wt.

%, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. % or 30 wt. % of the formulation. Most preferably, the gelling agent is present in the formulations in the weight concentration within a range of from and including 1 wt. % up to and including 5 wt. % of the formulation. It is selected from the gelling agents as used in the state of the art in the fields of pharmacy and cosmetics, as well as the food industry for the preparation of formulations in the form of gels, emulsions, creams and lotions and other similar forms.

Preferably, the gelling agent is selected from carbomers which are various polymers. The carbomer within the meaning of this invention means cross-linked acrylic acid homopolymers with high molecular weight. Most preferably, these are cross-linked polyacrylic acid polymers or 2-propenoic acid polymers that are polymers with 2,2-bis (hydroxymethyl)propane-1,3-diol 2-propenyl ether. Most preferably, a carbomer with the trade name Tego® Carbomer 140 manufactured by Evonik Nutrition & Care GmbH or a carbomer with the trade name Carbopol® Ultrez 10 Polymer manufactured by Lubrizol are used. It acts as a gel-forming agent, as a regulator or a viscosity control agent and a rheology modifier and emulsion stabiliser.

Within the meaning of this invention, suitable gelling agents also include acrylates such as:
 copolymer of acrylate and palmet-25 acrylate (also classified as acrylates/palmet-25-acrylate copolymer; e.g., a product with the trade name Synthalen® W2000 manufactured by 3V Inc. and 3V Group);
 polyacrylate cross-polymer 11 (e.g. a product with the trade name Aristoflex® Velvet manufactured by Clariant International Ltd.);
 synthetic polymers such as ammonium acryloyldimethyltaurate/VP copolymer (also classified as ammonium acryloyldimethyltaurate/VP copolymers; e.g., a product with the trade name Aristoflex® AVC manufactured by Clariant International Ltd.);
 cross-polymer of ammonium acryloyldimethyltaurate and behenet-25-methacrylate (also classified as ammonium acryloyldimethyltaurate/behenet-25-methacrylate cross-polymer; e.g., a product with the trade name Aristoflex® HMB manufactured by Clariant International Ltd.);
 hydroxypropyl cellulose (abbreviated form HPC; e.g., a product with the trade name Klucel™ manufactured by Ashland) that is a chemically processed natural cellulose polymer;
 hydroxypropyl methylcellulose (abbreviated form HPMC; e.g., a product with the trade name Walocel® HM 50 manufactured by Evonik) that is a chemically processed natural cellulose polymer;
 copolymer of hydroxyethyl acrylate and sodium acryloyldimethyltaurate (also classified as hydroxyethyl acrylate/sodium acryloyldimethyltaurate copolymer; e.g. a product with the trade name Sepinov™ EMT 10 manufactured by Seppic);
 Xanthan gum that is a fermented natural polysaccharide composed of pentasaccharide units of glucose, glucuronic acids and mannose in a molar ratio of 2:1:2.

In variant implementations and/or, if necessary, the formulation according to this invention also contains other or the so-called supplemental ingredients. These are selected from ingredients that include various oils, vitamins, fatty acids, minerals, active ingredients of plant origin, antioxidants and/or other similar ingredients. Each of the supplemental ingredients is present in the said formulation in a weight concentration within a range of from and including 0.01 wt. % up to and including 5 wt. % of the formulation and preferably in a concentration of either 0.01 wt. %, 0.02 wt. %, 0.03 wt. %, 0.04 wt. %, 0.05 wt. %, 0.06 wt. %, 2 wt. %, 0.07 wt. %, 0.08 wt. %, 0.09 wt. %, 0.1 wt. %, 0.15 wt. %, 0.20 wt. %, 0.25 wt. %, 0.3 wt. %, 0.35 wt. %, 0.4 wt. %, 0.45 wt. %, 0.5 wt. %, 0.6 wt. %, 0.65 wt. %, 0.7 wt. %, 0.75 wt. %, 0.8 wt. %, 0.85 wt. %, 0.9 wt. %, 0.95 wt. %, 1 wt. %, 1.5 wt. %, 2 wt. %, 2.5 wt. %, 3 wt. %, 3.5 wt. %, 4 wt. %, 4.5 wt. % or 5 wt. % of the formulation.

The oils as supplemental ingredients of the formulation are selected from oils such as olive oil, argan oil, jasmine oil, hemp oil, flaxseed oil, jojoba oil, coconut oil, avocado oil, various oils from citrus peel or the so-called oranol oil, babassu oil, sunflower oil, palm oil and various other vegetable oils, as they are known and used in the state of the art in the fields of cosmetics, pharmacy and food industry. Oils are used primarily in the formulations according to this invention that are in the form of an emulsion, milk, lotion, cream, gel and/or film dressing for the skin either on the face, arms, legs or for the whole body of the organism.

Vitamins as supplemental ingredients of the formulation are selected from vitamins, preferably vitamins A, C and/or E, while in alternative implementations of the formulations also vitamins D, K and/or B complex vitamins.

Alternatively, the formulation also contains fatty acids and, preferably, essential fatty acids, as supplemental ingredients of the formulation. Most preferably these are selected from omega 3 fatty acids.

Minerals as supplemental ingredients of the formulation are selected from minerals as they are known and used in the state of the art in the field of cosmetics, pharmacy and food industries. Most preferably, the minerals are selected from magnesium Mg, zinc Zn and/or selenium Se. These are preferably in the form of a citrate, chloride and/or carbonate.

The formulation according to this invention includes, as supplemental ingredients in the formulation, also various active ingredients of plant origin that are selected from active ingredients of plant origin as known and used in the state of the art in the fields of cosmetics, pharmacy and food industries. These active ingredients are preferably of natural and plant origins. Most preferably these include the active ingredients of ginger (*Zingiber officinale*), purple cornflower (*Echinacea purpurea*), myrrh (*Commiphora abyssinica*), marigold (*Calendula officinalis*), and/or St. John's wort (*Hypericum perforatum*), and other plants that are used according to the state of the art in the cosmetics, pharmacy and/or food industry as active ingredients of plant origin. The above stated active ingredients within the meaning of this invention are most preferably extracts from said plants and/or parts thereof. The function of the active ingredient of plant origin in the formulation is to formulate or moderate the effects of the formulation according to this invention. It is extremely preferable that such active ingredients of plant origin are selected from a combination of these, which are industrially or otherwise processed, such as e.g. extracts from plants or parts thereof. These are marketed under different names depending on the manufacturer and have, depending on the active ingredients, different effects on the target tissues, mucous membranes, structures and/or systems. For example, they are selected from among the products of the company Symrise AG under the trade name Actipone® that includes ginger (*Zingiber officinale*; namely an extract of its root), active ingredients of purple cornflower (*Echinacea purpurea*, namely its extract) and active ingredients of myrrh or myrtle (*Commiphora abyssinica*, namely an extract of its resin), which in addition to these active ingredients also contain, inter alia, water, glycerine, polysorbate, preservatives, sodium benzoate and/or potassium sorbate, and is recommended for use in a concentration of 0.02 wt. % to 0.65 wt. % of the formulation for anti-irritant or soothing effect, in a concentration of 1.25 wt. % for antioxidative effect and in a concentration of 1.05 wt. % to 4.20 wt. % for antimicrobial effect. The active ingredient of plant origin or, in other words, such active ingredients are present in the formulation in a weight concentration within a range of from and including 0.2 wt. % up to and including 5 wt. % of the formulation.

In variant implementations, the formulation according to this invention further comprises antioxidants as supplemental formulation ingredients that are selected from vitamins C, E and/or A and other antioxidant compounds, among which is preferably astaxanthin. The antioxidant astaxanthin is a fat-soluble xanthophilic carotenoid derived from some marine plants, mainly from Haematococcus pluvialis algae and/or from some marine animals such as salmons and shrimps, and from some other animals (e.g., trouts, flamingos, quails).

The formulation according to this invention further contains glycerine or glycerol, if necessary. Preferably, glycerine or glycerol or propylene glycol and/or other similar alcohols, as known and used in the state of the art as glycerol, are used in formulations in the form of gels, emulsions, creams, lotions and/or film dressings. When glycerine or any other similar ingredient is present in said formulations, it is present in concentrations ranging from including 0.2 wt. % up to and including 5 wt. % of the formulation, and preferably in a concentration of either 0.2 wt. %, 0.3 wt. %, 0.4 wt. %, 0.5 wt. %, 1 wt. %, 1.5 wt. %, 2 wt. %, 2.5 wt. %, 3 wt. %, 3.5 wt. %, 4 wt. %, 4.5 wt. % or 5 wt. % of the formulation.

When the formulation according to this invention is in the form of a formulation for oral care and care for oral cavity, its tissues, mucous membranes, structures and systems, including teeth, periodontal tissues (gingiva) and interdental spaces, it contains the following ingredients as listed and defined in this description and preferably further here as follows:

hydrogen peroxide as a key active ingredient and a source of active oxygen compounds in the formulation in a weight concentration within a range of from and including 0.5 wt. % up to and including 6 wt. % of the formulation;

silver in ionised and colloidal form and/or gold in ionised and colloidal form, another key active ingredient in the formulation with the function of a mild antiseptic agent, namely, in a weight concentration within a range of from and including 0.1 wt. % up to and including 4 wt. % of the formulation;

aloe vera as a passive ingredient or a component in the formulation with a mucosal care function in a weight concentration of the formulation within a range of from and including 0.2 wt. % up to and including 10 wt. % of the formulation;

hyaluronic acid or its sodium salt, sodium hyaluronate, as a passive ingredient or a component in the formulation with the function of a moisturiser or humectant and mucosal care function, and, if necessary, any other additional moisturiser so that the total share of moisturisers in the formulation is in a weight concentration within a range of from and including 0.2 wt. % up to and including 10 wt. % of the formulation;

if necessary, panthenol that is present in the formulation in a weight concentration within a range of from and including 0.2 wt. % up to and including 10 wt. % of the formulation;

if necessary, one or more flavours that are present in the formulation in a weight concentration within a range of from and including 0.05 wt. % up to and including 1 wt. % of the formulation. Such flavours are selected from those used in the state of the art in the fields of cosmetics, pharmacy and food industry for use in oral cavity. Most preferably, such flavour is selected from flavours such as spearmint and/or stevia;

if necessary, one or more fragrances or one or more perfumes that are present in the formulation in a weight concentration within a range of from and including 0.01 wt. % up to and including 3 wt. % of the formulation. Such fragrances are selected from those used in the state of the art in the fields of cosmetics, pharmacy and food industry for use in oral cavity;

if necessary, a gelling agent for certain forms of formulations that is present in the formulation in a weight concentration within a range of from and including 1 wt. % up to and including 30 wt. % of the formulation;

if necessary, supplemental ingredients including various oils, vitamins, fatty acids, minerals, active ingredients of plant origin and antioxidants and/or other similar ingredients as defined herein. These ingredients are present in the formulation in a single weight concentration, i.e. with respect to a single ingredient, when it is present alone, or in a total weight concentration of all these supplemental ingredients within a range of from and including 0.01 wt. % up to and including 5 wt. % of the formulation;

if necessary, glycerine or glycerol or propylene glycol and/or other similar alcohols, whether alone or in combination with other such ingredients, namely in a single weight concentration, i.e. with respect to each such ingredient, when present alone, or in a total weight concentration of all such ingredients within a range of from and including 0.2 wt. % up to and including 5 wt. % of the formulation.

The subject matter of this invention are in addition to the various types and forms of formulations by composition or ingredients and physical form of the formulation such as solution, mouthwash (mouth rinse), spray, gel, paste, emulsion, lotion, milk, and/or cream, also various controlled release formulations of active ingredients such as film dressings, liposomes and/or mycelia, as well as the said formulations included in the applicators or devices for application of this formulation to and/or into the target area of the organism that are preferably selected from patches, dental shower devices together with various shower toothbrushes such as spray toothbrush, rotary and interdental toothbrush, other toothbrushes and/or interdental toothbrushes and other accessories, as they are known and used in the state of the art for this purpose.

In addition, the subject matter of this invention are also procedures for preparation or production of said formulations and devices that include these formulations for their application or use on and/or in target areas of the organism.

Through these procedures, a semi-finished formulation is prepared first in the form and composition as defined in this invention and in the physical form of the formulation selected from the forms such as a solution, mouthwash, spray, gel, paste, emulsion, lotion, milk, cream and/or liposomes and mycelia and/or such formulation to formulate or form a film dressing at the target site of activity. A semi-finished formulation within the meaning of this invention is a formulation according to this invention prior to being packaged in packaging of different sizes with different gram and/or volume contents of the formulation in the packaging, whereby the packaged formulation in such packaging constitutes the end product within the meaning of this invention. Preferably, the semi-finished product within the meaning of this invention is a formulation with active oxygen compounds and other active ingredients and ingredients described herein that is then filled into storage containers and stored until the production stage of the product that is the final product.

The product within the meaning of this invention is the end product, i.e. a semi-finished product that is filled, dosed and packaged into a final product intended for use by users of such products.

The production procedure of a formulation with active oxygen compounds according to this invention includes the following steps:
  a) production of a semi-finished product that includes the following steps:
    first basic components of the active oxygen compounds are produced and prepared from hydrogen peroxide;
    this is followed by filtration and stabilisation of hydrogen peroxide with stabilisers for nutritional use;
    this is followed by dosing or weighing of the basic raw material of hydrogen peroxide into the mixing reactor and continuous stirring with the gradual addition of the active ingredients and ingredients of the formulation of this invention according to the increasing density rule, thus preparing a semi-finished product;
    testing of the semi-finished product with regard to pH-value, hydrogen peroxide concentration and, if necessary, density of the semi-finished product that was prepared in this way;
    the free-fall outflow of the semi-finished product from the mixing reactor into a prepared storage container sealed to prevent access of oxygen, air and other environmental elements;
    storage of the semi-finished product in the storage container until it is filled into packaging in an environment free of air, oxygen and/or other gases and/or other environmental elements;
  b) production of the final product that includes the following steps:
    filling a semi-finished product into packaging and the packaging process.

More specifically, the production procedure of a formulation with active oxygen compounds according to this invention includes the following stages and steps:
  First the basic components of the active oxygen compounds are produced and prepared from hydrogen peroxide. Hydrogen peroxide is prepared according to procedures known in the state of the art. This is followed by filtration and stabilisation of hydrogen peroxide with stabilisers of high purity and safety that are also suitable for nutritional use or in short, the so-called food grade stabilisers that are selected from the hydrogen peroxide stabilisers used in the food industry for the purposes of food products. In this case, hydrogen peroxide is prepared in a mixing reactor that is purified before the production of the semi-finished product according to a procedure known in the state of the art and includes the protection of the mixing reactor by the procedure for protection against the effects of oxidation of the active oxygen compounds.

Thereafter, the basic raw material of hydrogen peroxide is dosed or weighed into the mixing reactor in a weight concentration of from and including 32 wt. % up to and including 37 wt. % of hydrogen peroxide relative to the desired concentration of the active ingredient in the formulation within the meaning of this invention and is stirred in the mixing reactor at a corresponding rate (specifically determined number of rotations). Other ingredients/raw materials of the formulation, i.e. auxiliary ingredients or adjuvants of the formulation are gradually added to hydrogen peroxide in the mixing reactor in amounts to achieve the desired concentrations of these ingredients in the formulation within the range that is within the scope of this invention. In this case, the individual ingredients of the formulation are pre-dosed or weighed on a scale, that is preferably electronic, but it can also be any other calibrated scale as used in the state of the art to weigh the ingredients of the formulation within the meaning of this invention. The above stated auxiliary ingredients or adjuvants are gradually added to said mixing reactor with continuous mixing.

After mixing in all the ingredients of the formulation, a sample of the semi-finished formulation product is taken and is analysed in the laboratory. The pH, the concentration of hydrogen peroxide and, if necessary, the density of the prepared semi-finished product are measured.

After carrying out the analysis of the sample of the semi-finished product, the semi-finished product is drained in free fall from the mixing reactor into a prepared storage container sealed against access of oxygen from the air to prevent oxidation of the semi-finished product. In this container the semi-finished product, i.e. the pre-prepared formulation, which is waiting to be filled into the final packaging, is stored until filling into the packaging in an environment free of air, oxygen and/or other gases and/or other environmental elements.

The preparation and storage of the semi-finished product is followed by the preparation of the final product.

The production of a final product includes filling a semi-finished product into packaging and the packaging process. It is performed on the filling lines and by using the filling lines and machines and under the conditions of setting the filling and packaging parameters, whereby the filling lines and machines are selected from the filling lines and machines that are used for the purposes of filling and packaging of various types of formulations in the form of solution, gel, emulsion, lotion, milk and/or cream. The conditions for setting the semi-finished product filling and packaging parameters within the meaning of this invention, among which are the conditions for setting the parameters as known in the state of the art, and preferably in the field of cosmetic products, and among which, for example, are classified and are not limited to the here listed e.g. the volume of filling the formulation into the final product with a specific volume of packaging, pressure or filling pressure, product labelling, etc. It is key here that the filling line is cleaned, neutralised and disinfected before each start of filling and packaging procedure, as it is known in the state of the art for filling and packaging of products containing hydrogen peroxide or active oxygen compounds as active ingredient.

In addition, the final product of the formulation according to this invention is also a formulation contained in various devices for care for and maintenance and preservation of a healthy condition of the tissues, systems and structures of skin, nails (finger- and toenails) and oral cavity as referred to herein. Such final products of the formulations according to this invention include, inter alia, various forms of formulations which are, for the purpose of controlled release of the active ingredients and ingredients according to this invention, included in devices that are selected from patches, dental showers, toothbrushes and/or interdental toothbrushes.

Furthermore, the subject matter of this invention are procedures for production of devices according to this invention that include these formulations for their application or use on and/or in target areas of the organism.

Said formulation may also be used to facilitate care for minor injuries of skin and nails (finger- and toenails) that are shallower and do not include major inflammations and infections, among which are classified but are not limited to the ones listed herein, such as minor mechanical and/or thermal injuries and minor injuries resulting from physical or mechanical, biological and/or microbiological injuries, among which are also skin lesions with a slight or minor or less extensive bleeding. Injuries that are deeper and include subcutaneous tissues, structures and systems and/or those that have intense and/or major bleeding are excluded here.

Minor or shallower mechanical injuries within the meaning of this invention are caused by different mechanical forces. For example, these wounds within the meaning of this invention include shallower and/or smaller areas of the human body such as wounds, abrasions or scratches, tears, cuts or gashes, punctures or stab wounds, of any origin, bite wounds caused by bites or pecks of various animals (e.g. dogs, cats, pigs, horses, cows, chickens, birds, rats and mice, and other rodents and other mammals). These wounds also include gunshot or bullet wounds or grazes (e.g., grazing and tangential shot wounds, in which a projectile grazes a part of the body and causes shallower injuries and/or wounds that have a grooved or other similar shape.

Minor or shallower heat injuries within the meaning of this invention are cause by high-temperature heat and/or hot objects and/or high-temperature environmental factors and/ or because of cold or cold objects and/or low-temperature objects and/or environmental factors. Such injuries include minor and/or shallower burns and/or frostbite that cover a smaller surface area of the human body.

Wounds or injuries to the tissues, mucous membranes, systems and structures within the meaning of this invention are characterised by interruptions of the continuity of the skin and/or mucous membrane and/or nail (finger- or toenail) and/or tooth that are either the result of a violent, negligent, inadvertent act due to recklessness and/or carelessness, and are either free of or with defects of the structures, tissues and/or systems-under the skin, the mucosa, nail (finger- or toenail) and/or tooth. Within the meaning of this invention, these wounds or injuries are superficial and cover smaller surfaces and do not include the entire surface of the body. In case of such wounds or injuries exuding of lymphatic fluid, interstitial fluid and/or mild small-scale bleeding can occur, and in some cases infections of various types. In case of wounds or injuries, infections can ensue because the objects that caused them and or the ambient factors are infected.

Hydrogen peroxide and active hydrogen compounds according to this invention oxygenate and regenerate the target area of the organism and preferably the target tissue, mucous membranes, structures and systems of the organism that preferably include the skin, subcutaneous tissues, mucous membranes (mucosa), structures and systems, including nails (finger- and toenails) and cuticle tissues (tissues around nails or cuticle), both on the surface of the body, in the subcutaneous tissues as well as in the ear cavity or in the ears, and tissues, mucous membranes, structures and systems in the oral cavity, including teeth, periodontal tissues (gingiva or tissues around tooth and/or teeth) and interdental spaces.

When the formulation comes into contact with the surface of the skin, with tissues, mucous membranes, structures and systems of integumentary systems and subcutaneous systems, including nails (finger- and toenails) and cuticle tissues (tissues around nails or cuticle), and of the ears and ear cavities, and/or with the surface of the oral cavity and/or with tissues, mucous membranes, structures and systems of the oral cavity, including teeth, periodontal tissues (gingiva) and interdental spaces, the formulation releases oxygen bubbles, due to which the formulation lightly foams on the application surface. Released oxygen thus causes oxygenation of the target tissues, mucous membranes, structures and/or systems that are either healthy, injured and/or inflamed, removes the debris and exudate or discharge from the area of possible inflammation or injury, thereby contributing to the regeneration and renewal of said target tissues, mucous membranes, structures and/or systems. In addition to the above, the released oxygen dissolves ear wax in the ears and thus helps to remove it.

When the formulation comes into contact with the surface of the teeth, oxygen bubbles are released from the formulation, whereby the formulation lightly foams on the application surface, removing food residues, dental plaque and/or tartar from the surface of the teeth and periodontal tissues (gingiva) and from the interdental spaces without affecting the solidity and/or structure of the enamel. This way, the formulation according to this invention helps to remove food residues, dental plaques and tartar, prevents them from congesting and depositing on and/or in the targeted areas in the oral cavity, and helps to prevent inflammation and bleeding in the oral cavity, periodontitis and periodontal disease.

The released oxygen thus causes oxygenation and removes debris and exudate or discharge from the area of possible inflammation or injury.

Passive ingredients hydrate, regenerate and nourish the target tissue, structures and systems of the skin, nails (finger- and toenails) and cuticle tissue and mucous membranes or tissue, structures and systems in the oral cavity. In addition, the passive ingredients as well as the active oxygen compounds within the meaning of this invention have a mildly antiseptic effect on said target tissues, structures and systems, thereby providing protection against pathogenic microorganisms, i.e. against bacteria, fungi, viruses and other microorganisms.

IMPLEMENTATION EXAMPLES

A Procedure for Producing Formulations with Active Oxygen Compounds in Gel Form

With this procedure, a semi-finished formulation in gel form is prepared that means a semi-finished product prior to being packaged in packaging of different sizes with different gram and/or volume contents of the formulation in the packaging, whereby the packaged formulation in gel form in such packaging constitutes the end product within the meaning of this invention.

The procedure described herein is used for the preparation of formulations with active oxygen compounds whose key source in the formulations within the meaning of this invention is hydrogen peroxide, whereby formulations are in gel form having different contents of individual ingredients within the concentration range according to this invention. The concentrations specified here refer to the weight shares and/or percentages or wt. % by weight of each ingredient with regard to the weight of the total formulation in gel form.

Thus, gels or formulations in gel form that are prepared in this way contain:

hydrogen peroxide that is a key active ingredient in formulations within the range of from 0.5 wt. % to 6 wt. % of the formulation;

hyaluronic acid or its sodium salt for use as a humectant and skin care agent and, if necessary, a supplemental moisturiser, such as glycerine or glycerol and/or propylene glycol, that binds water and facilitates maintenance of the proper humidity level of the formulation. These ingredients are dosed individually or in a total concentration within the concentration range of from 2 wt. % to 10 wt. % of the formulation. Preferably, the sodium salt of hyaluronic acid or sodium hyaluronate is used;

aloe vera within the range of from 0.2 wt. % to 10 wt. % of the formulation. It acts as a skin softener and moisturiser;

ionic or ionised silver (Ag) in colloidal form within the range of from 0.1 wt. % to 4 wt. % of the formulation and/or ionic or ionised gold (Au) in colloidal form within the range of from 0.1 wt. % to 4 wt. % of the formulation, whereby the formulation in the case of a combination of the two includes the total proportion (share) of both that is also within the range of from 0.1 wt. % to 4 wt. % of the formulation. Individually or together, they act as a mild antiseptic agent;

carbomer gelling agent within the range of from 1 wt. % to 30 wt. % of the formulation. Carbomer is a 2-propenoic acid that is a polymer with 2,2-bis(hydroxymethyl)propane-1,3-diol 2-propenyl ether. It acts as a gel-forming agent, as a regulator or a viscosity control agent and as an emulsion stabiliser;

if necessary, a buffer that is either a triethanolamine and/or NaOH and is used to neutralise the gel. Triethanolamine is also called trolamine and is chemically 2,2',2"-nitrileotriethanol and acts as a buffer or a pH-value balancer;

if necessary, panthenol within the range of from 0.2 wt. % to 10 wt. % of the formulation;

if necessary, a perfume, one or a combination of more than one perfume, within the range of from 0.01 wt. % to 3 wt. % of the formulation;

Weigh all the necessary raw materials that are ingredients of the formulation in gel form into properly prepared weighing containers in quantities to achieve the target concentration of these ingredients in the gel formulation.

All liquid raw materials used for gel preparation are pre-filtered through a filter with 200 μm pores.

In a 5% volume of total hydrogen peroxide, an appropriate quantity of sodium hyaluronate is first added to this mixture, the mixture is then mixed and homogenised with a mixing device selected from those known in the state of the art, and is preferably a Dynamix® 160 mixing device. The mixture is stirred for so long and at such a stirring speed that a homogeneous mixture is obtained. Preferably, mixing is carried out for 5 minutes at a speed of 2000 revolutions per minute (hereinafter referred to as: rpm).

Then, sequentially add to and mix in the homogeneous mixture of hydrogen peroxide and sodium hyaluronate contained in the reactor, as described in the above defined procedure of preparation of formulation in solution form, individual ingredients following the sequence of steps as described below. The procedure of adding and mixing in the other ingredients of the formulation is carried out in the sequence of the following steps and using the process parameters as follows:

The residual hydrogen peroxide is first added to the homogenised mixture of hydrogen peroxide and sodium hyaluronate in the above stated reactor device.

Then a solution of sodium hyaluronate with the remaining amount thereof is added to this mixture in the reactor with respect to the target sodium hyaluronate content in wt. % in the final formulation and stirred for 1 minute at 2000 rpm.

This is followed by mixing in aloe vera and glycerine into the reactor and homogenising for 2 minutes at 2000 rpm.

Then ionised silver and/or ionised gold in colloidal form is added into this mixture in the reactor and homogenised for 10 seconds at 4000 rpm.

Thereafter, one or more flavours and, if necessary, one or more perfumes are added into this mixture in the reactor and the whole mixture is homogenised for 5 minutes at 2000 rpm.

This is followed by the addition of carbomer and homogenisation of the mixture for 5 minutes at 2000 rpm.

Finally, the resulting mixture is neutralised with the addition of triethanolamine and/or NaOH buffer by mixing for 2 minutes at 200 rpm.

If necessary, the sequence of steps described above may also be changed and/or, if necessary, individual parameters in the above defined steps of the procedure may also be changed, insofar this does not significantly affect the stability, efficacy and/or form of the target formulation.

A Procedure for Producing Formulations with Active Oxygen Compounds in Solution Form With this procedure, a semi-finished formulation in solution form that means a semi-finished product prior to being packaged in packaging of different sizes with different gram and/or volume contents of the formulation in the packaging, whereby the packaged formulation in solution form in such packaging constitutes the end product within the meaning of this invention.

The procedure described below applies to the preparation of formulations with active oxygen compounds within the meaning of this invention that are in the solution form with varying contents of individual ingredients within the concentration range according to this invention. The concentrations specified here refer to the weight shares and/or percentages or wt. % by weight of each ingredient with regard to the weight of the total formulation in solution form. The active ingredients and ingredients of the formulation are added by increasing density rule, i.e., the ingredients of lesser density are added first and then the denser ingredients are added and finally the densest ingredient.

The solutions or formulations in solution form thus prepared contain the following:

hydrogen peroxide that is a key active ingredient in formulations within the range of from 0.5 wt. % to 6 wt. % of the formulation;

hyaluronic acid or its sodium salt within the range of from 0.2 wt. % to 10 wt. % of the formulation. Preferably, the sodium salt of hyaluronic acid or sodium hyaluronate is used. They act as a moisturiser or humectant and a skin care agent;

aloe vera within the range of from 0.2 wt. % to 10 wt. % of the formulation. Aloe vera is a herbal substance obtained from the leaves of the plant *Aloe barbadensis* and acts as a skin care agent, moisturiser and skin softener;

ionic or ionised silver (Ag) in colloidal form within the range of from 0.1 wt. % to 4 wt. % of the formulation and/or ionic or ionised gold (Au) in colloidal form within the range of from 0.1 wt. % to 4 wt. % of the formulation, whereby the formulation in the case of a combination of the two includes the total proportion (share) of both that is also within the range of from 0.1 wt. % to 4 wt. % of the formulation. They act as a mild antiseptic agent;

flavour within the range of from 0.01 wt. % to 1 wt. % of the formulation;

if necessary, panthenol within the range of from 0.2 wt. % to 10 wt. % of the formulation;

if necessary, a perfume within the range of from 0.01 wt. % to 3 wt. % of the formulation.

Weigh all the necessary raw materials that are ingredients of the formulation in solution form into properly prepared weighing containers in quantities to achieve the target concentration of these ingredients in the solution formulation.

All liquid raw materials used for preparation of the solution are pre-filtered through a filter with 200 micron pores (hereinafter referred to as: μm).

In a 5% volume of total hydrogen peroxide, an appropriate quantity of sodium hyaluronate is first added to this mixture, the mixture is then mixed and homogenised with a mixing device selected from those known in the state of the art, and is preferably a Dynamix® 160 mixing device. The mixture is stirred for so long and at such a stirring speed that a homogeneous mixture is obtained. Preferably, mixing is carried out for 5 minutes at a speed of 2000 revolutions per minute (hereinafter referred to as: rpm).

Then, sequentially add to and mix in the homogeneous mixture of hydrogen peroxide and sodium hyaluronate contained in the reactor individual ingredients following the sequence of steps as described below. The reactor within the meaning of this invention is a chemical reactor selected from the reactors as known and/or used in the state of the art. It is a process device for carrying out chemical reactions or processes under different conditions of reaction parameters, such as temperature, pressure, different purity and/or the presence and/or absence of air and/or other gases that has various shapes and sizes of volume and is made of different materials depending on the requirements of the processes or reactions, and, if necessary, includes additional functional elements to perform various reactions/processes, such as various mixers, thermostats, etc.

The procedure of adding and mixing in the other ingredients of the formulation is carried out in the sequence of the following steps and using the process parameters as follows below.

The hydrogen peroxide is first added to the homogenised mixture of hydrogen peroxide and sodium hyaluronate in the above stated reactor device.

Then a solution of sodium hyaluronate with the remaining amount thereof is added to this mixture in the reactor with respect to the target sodium hyaluronate content in wt. % in the final formulation and stirred for 1 minute at 2000 rpm.

This is followed by mixing in aloe vera into the reactor and homogenising for 2 minutes at 2000 rpm.

Then ionised silver and/or ionised gold in colloidal form is added into the reactor and homogenised for 10 seconds at 4000 rpm.

Thereafter, one or more flavours and/or, if necessary, one or more perfumes are added into this mixture in the reactor and the whole mixture is homogenised for 5 minutes at 2000 rpm.

If necessary, the sequence of steps described above may also be changed and/or, if necessary, individual parameters in the above defined steps of the procedure may also be changed, insofar this does not significantly affect the stability, efficacy and/or form of the target formulation.

An Implementation Example of Preparation of Liposomes for Formulations in the Form of Liposomes with Controlled Release of Active Oxygen Compounds and Procedure of Its Preparation The formulation in liposome form consists of liposomes that have at their core a micro-formulation according to this invention with active oxygen compounds, i.e. a formulation comprising hydrogen peroxide molecules in a weight concentration of the entire formulation of from and including 1 wt. % up to and including 6 wt. % of hydrogen peroxide and/or alternatively benzoyl peroxide and/or carbamide peroxide molecules in a weight concentration of the entire formulation of from and including 5 wt. % up to and including 20 wt. % of benzoyl peroxide or carbamide peroxide and, if necessary, peroxidase enzyme, preferably glucose oxidase. The micro-formulation is in gel form that in addition to said active ingredient also contains hyaluronic acid, panthenol and Actipone® as described herein.

The liposomes described herein and prepared according to this procedure are then incorporated into the formulations according to this invention that are in the form of gels, creams, emulsions and/or pastes according to this invention and include other active ingredients and auxiliary ingredients or adjuvants within the meaning of this invention as defined in this description of the invention.

Production of Liposomes

According to this invention, the liposomes have active oxygen compounds embedded in the liposome core or nucleus. According to this invention, the liposomes are within the size range of 25 nm to 1000 nm, and preferably in the range of 100 nm to 500 nm.

Preferably, the source of the active oxygen compounds is hydrogen peroxide according to this invention and, alternatively, benzoyl peroxide or carbamide peroxide that is embedded in the nucleus or the core of the liposome, into the membrane of which a peroxidase enzyme is embedded, if necessary, which catalyses its degradation into active oxygen compounds. Instead of the stabilised hydrogen peroxide according to this invention, alternatively benzoyl peroxide or carbamide peroxide may be selected.

Liposomes are produced by a reverse phase evaporation procedure as is known and used in the state of the art. Preferably, this is the procedure of F. Szoka and D. Papadjopolous, as described in Proc. Natl. Acad. Sci. 75 of 1978 on pages 4194-4198 by mixing phosphatidyl inositol compounds (hereinafter referred to as abbreviation: PI) and dimiristoylphosphatidylcholine (hereinafter referred to as abbreviation: DMPC) at a ratio of 1:9 together with an aqueous solution of the enzyme glucose oxidase. Instead of dimiristoylphosphatidylcholine (hereinafter referred to as abbreviation: DMPC) dipalmitoylphostatidylcholine (abbreviation: DPPC) or distearoylphosphatidylcholine (abbreviation: DSPC) can also be used.

To 9 mg of DMPC was added 1 mg of PI and 100 μl of DPPC and 3 ml of a mixture of distilled chloroform and methanol at a ratio of 4:1. The mixture was evaporated at 60° C. by rotation to obtain a thin lipid film. This was dispersed in 6 ml mixture of distilled chloroform and methanol at a ratio of 4:1 and 3 ml of 1/10 nitrogen saturated phosphate-buffered brine solution in a concentration of 0.15 mol/l (hereinafter referred to as: PBS) that contained 10 mg of glucose oxidase. The mixture was mixed by rotation and sonicated for 4 min in a bath sonicator under nitrogen and at a bath temperature of 30° C., which is the temperature above the lipid phase transition, i.e. of phospholipid, more specifically phosphatidylcholine. Preferably, the procedure was performed on a sonicator manufactured by Decon Ultrasonics Ltd. (Sussex, England) using the Decon FS 100 device. Through this mixing a homogeneous emulsion was obtained which, when rotated, was evaporated at a temperature above the phase transition of said lipid. First, a viscous lipid gel phase was formed, and then a gel inversion occurred when an aqueous lipid suspension was formed. It was purified by help of oxygen during exposure to nitrogen for 15 min at a temperature above the lipid phase transition. This way the traces of organic solvents were eliminated while, at the same time, any defects in the formation of the liposomal membrane and the liposomes themselves were eliminated as well.

In the case of using DPPC, instead of DMPC, a bath temperature of 50° C. was used, and in the case of DSPC, a bath temperature of 60° C. was used, which is the phase transition temperature of said lipid.

To remove the glucose oxidase enzyme from the suspension thus formed that was not incorporated in the liposomes and floated freely in suspension, this was removed by purification by the procedure of Sepharose 4B column chromatography (30×1.5 cm), where the column was previously purified with liposome dispersion in order to prevent liposome adsorption on the surface of the Sepharose gel matrix. The chromatography was performed during flushing using PBS (i.e. phosphate buffered brine solution) with a pH-value of 7.3 at a flow rate of 0.2 ml/min. Through this purification, fractions of the purified suspension were collected in a quantity of 2 cm$^3$.

The liposomes thus produced are shown in FIG. 1 that shows schematically simplified the liposome with the formulation according to this invention as one of the implementation examples of the formulation within the meaning of this invention. Such formulation is in the form of liposomes for use in the oral cavity or on the skin with controlled release of active oxygen compounds at the target area of the organism.

FIG. 1 schematically shows such a liposome with the formulation that contains active oxygen compounds according to this invention as one of the implementation examples of the formulation within the meaning of this invention. Such formulation is in the form of liposomes for use in the oral cavity or on the skin with controlled release of active oxygen compounds, which is achieved in the oral cavity by the effect of saliva and ambient temperature of the oral cavity on liposomes, or on the skin by the effect of exudate on the skin and ambient temperature on liposomes, including skin temperature. If necessary, a peroxidase enzyme is present in the liposome envelope or membrane for faster release of active oxygen compounds. The source of active oxygen compounds as the key or main active ingredient is stabilised hydrogen peroxide (chemical formula: $H_2O_2$) according to this invention, and alternatively benzoyl peroxide (chemical formula: $C_{14}H_{10}O_4$) or carbamide peroxide instead of hydrogen peroxide.

The liposome shown in FIG. 1 within the meaning of this invention has an envelope or the so-called membrane consisting of phospholipid molecules. Each phospholipid molecule has a polar part or the so-called polar head 1 with hydrophilic properties, and a two-pointed lipophilic or hydrophobic part or the so-called hydrophobic tail 2. The phospholipid molecules in the membrane of the liposome are structured and oriented so that one membrane lamella, i.e. the outer layer with polar heads 1 is arranged on the outside of the liposome and with hydrophobic tails 2 oriented towards the centre of the liposome membrane, and that the second membrane lamella, i.e. the inner layer with polar heads 1 is arranged on the inside of the liposome, i.e. at the nucleus or core of the liposome and with hydrophobic tails 2 oriented towards the liposome membrane core. The liposome has a hydrophilic layer or hydrophilic microenvironment both on the outside of the liposome as well as along and in the nucleus/core of the liposome and a hydrophobic layer or hydrophobic microenvironment within the liposome membrane next to the tails 2. In the nucleus or the core of the liposome is a micro-formulation according to this invention with active oxygen compounds, i.e. a formulation that includes hydrogen peroxide molecules or alternatively benzoyl peroxide or peroxide carbamide molecules in a gel medium. If necessary, the peroxidase enzyme 4 is present in the liposome membrane.

FIG. 2 schematically shows the structure of a double-layer phospholipid membrane or liposome envelope, as shown in FIG. 1, which consists of a series of phospholipid molecules oriented in space so that the polar or hydrophilic heads 1 of these molecules on one side and the hydrophobic or non-polar tails 2 of phospholipids contact each other.

Implementation Example of Mycelium Structure for Formulations in Mycelia Form with Controlled-Release of Active Oxygen Compounds FIG. 3 schematically shows a mycelium with a formulation that contains active oxygen compounds according to this invention as one of the implementation examples of the formulation within the meaning of this invention. Such formulation is in the form of mycelia for use in the oral cavity or on the skin with controlled release of active oxygen compounds, which is achieved in the oral cavity by the effect of saliva and ambient temperature of the oral cavity on mycelia, or on the skin by the effect of exudate on the skin and ambient temperature on mycelia, including skin temperature.

FIG. 4 schematically shows the structure of a single-layer phospholipid mycelium envelope, as shown in FIG. 3, consisting of a series of phospholipids with hydrophilic heads 1 on the external side of the mycelium and with hydrophobic tails 2 on the internal side of the mycelium, where active oxygen compounds within the meaning of this invention are placed in the mycelium core in micro-formulation in gel form that is the same as in the above described implementation example of the liposomal form of micro-formulation.

An Implementation Example of a Patch According to this Invention in the Form of Liposomes FIG. 5 schematically shows one of the implementation examples of the patch with the formulation according to this invention for use on skin and integumentary systems where the active oxygen compounds that are contained in the liposomes of the gel medium and which are together with other ingredients of the formulation embedded in the pad or matrix O1 of the patch, are released in a controlled manner over a certain time period. This occurs under the influence of the effect of the ambient temperature and other elements on the target part or site of the organism, which are substances and other elements on the surface of the skin such as exudate and its ingredients. Alternatively, a patch with such a structure can also be used for the oral cavity.

The matrix of patch O1 is attached on the holder of patch O2 that has an adhesive layer of silicone or similar polymers applied to the edge of the holder for attachment of the patch to the target site of the organism. At the same time, the figure shows the direction of release of active ingredients and other ingredients of the formulation to the target site of the organism. This direction is symbolically represented by the wide arrow O3 pointing downwards or out from the patch matrix O1. The direction of the effect of ambient temperature and other elements, such as exudate, on the skin and mucous membranes, or alternatively saliva in the oral cavity is symbolically shown by the broad arrow O4 pointing upwards or into the patch matrix O1.

Figure 6:
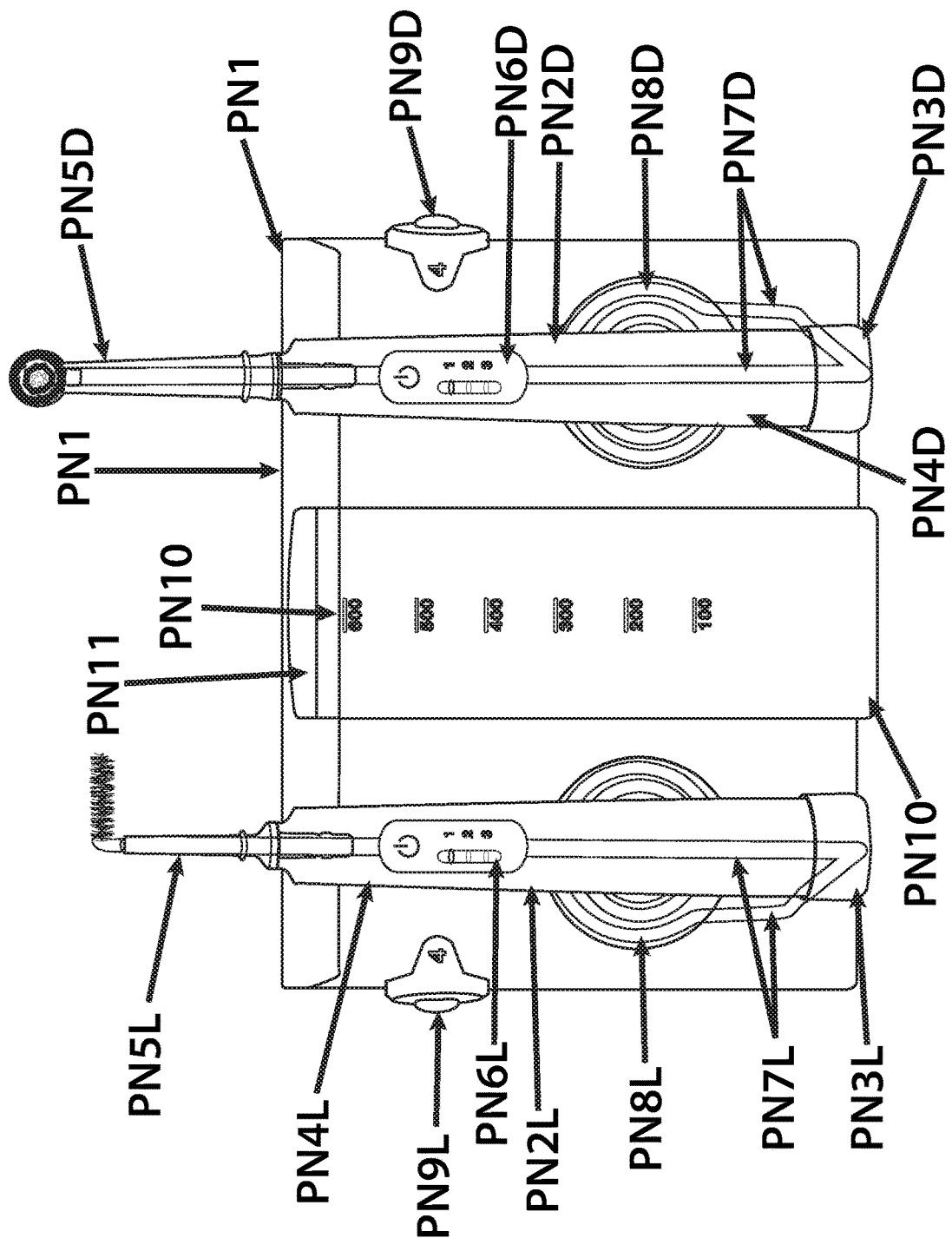
FIG. 6 schematically shows the applicator or device for the application of the formulation according to this invention on the target site of the organism, which is the oral cavity with teeth and its associated tissues, mucous membranes, structures and systems. The device shown is a dental shower device that has a container with the formulation according to this invention, two separate delivery tubes that are connected to two spray toothbrushes for use in the oral cavity with an interchangeable toothbrush heads mounted in the toothbrush handle. The left toothbrush has a mounted interdental toothbrush head that is shown in more detail in FIGS. 7 and 8. The right brush has a mounted rotating toothbrush head for oral cavity, that is shown in more detail in FIGS. 9 and 10, for cleaning teeth, periodontal tissues (gingiva) and spaces and other structures in the oral cavity, including the tongue, and thereby also for removing plaque and residues of food and beverages. The figure shows a front view of the dental shower device.

The Implementation Example of the Dental Shower Device with Interchangeably Adjustable Spray Brushers of Various Designs and Functions for Controlled Application of the Formulation According to the Present Invention, and Thus the Release of Active Oxygen Compounds FIG. 6 schematically shows the applicator or device for the application of the formulation according to this invention on the target site of the organism, which is the oral cavity with teeth and its associated tissues, mucous membranes, structures and systems. The device shown is a dental shower device PN1 that is equipped with a formulation container PN10 according to this invention that is preferably in the form of a solution, mouthwash and/or spray. A container PN10 which has a cover PN11 over an aperture for pouring in of the formulation according to this invention. The container PN10 is connected with two dental shower toothbrushes PN2L and PN2D for use in the oral cavity via two separate feed tubes PN7L and PN7D that are for the purpose of extending the distance between the device and the toothbrush during oral cavity cleaning screwed onto threads PN8L and PN8D, and are in this illustration visible only on the front external side of the device and are shown schematically due to the intelligibility of the placement of the tube also with symbolic illustrations in lighter grey colour in their running from the thread PN8L and PN8D through the brush stand PN3L or PN3D, the brush handle PN4L or PN4D and the brush head PN5L or PN5D.

Through the feed tubes PN7L and PN7D, also shown in the thread PN8L and PN8D for extending the distance between the device and the brush handle up to a length of from and including 20 cm up to and including 70 cm, flows the formulation according to this invention from container PN10 via the handle stand PN3L or PN3D, via the brushes PN2L or PN2D and this handle PN4L or PN4D to the spray nozzles in the brush heads PN5L or PN5D. The heads of these brushes have a tube integrated in the centre for flow of the formulation to the spray nozzles, where, when attaching or fitting the brush head to the brush handle PN4L or PN4D, the brush head tube PN5L or PN5D is fixed to and connected with the device feed tube PN7L or PN7D.

The shower brushes in FIG. 6 are fitted with different heads PN5L and PN5D that are interchangeable onto the brush handles. The left brush is fitted with an interdental brush head PN5L that is shown in more detail in FIGS. 7 and 8, and thus adjusted or installed acts as an interdental toothbrush. The right brush has a mounted rotating brush head PN5D for the oral cavity that is shown in more detail in FIGS. 9 and 10, and thus adjusted or installed acts as a rotating toothbrush for cleaning teeth, periodontal tissues (gingiva) and spaces and other structures in the oral cavity, including the tongue, and thereby for removing plaque and residues of food and beverages.

For each toothbrush, the device has a separate adjustment button PN5L and PN9D on the side edges for speed regulation and thereby formulation feed volume. Each toothbrush handle has an adjustment button PN6L or PN6D to regulate the speed of rotation and/or vibration of the toothbrush head. The toothbrush handle PN4L or PN4D is positioned on the stand of the handle PN3L or PN3D.

Figure 7:
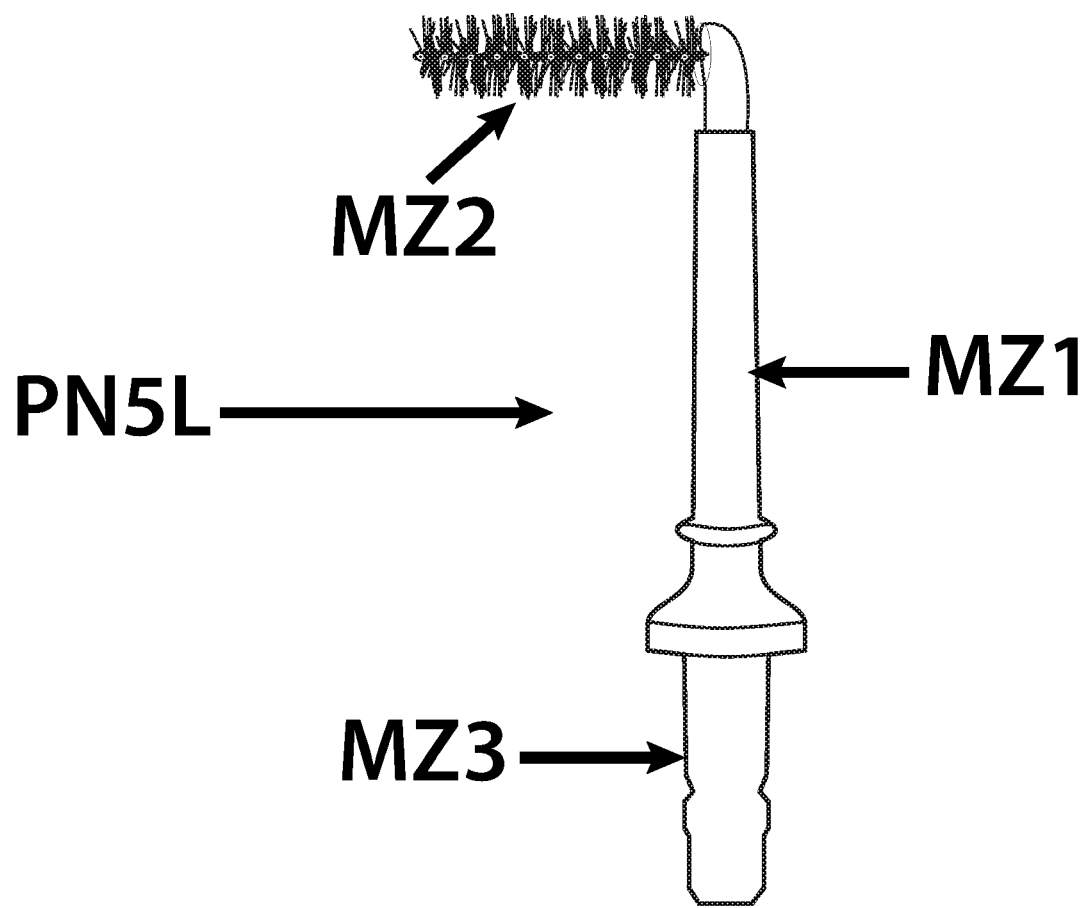
FIG. 7 schematically shows in more detail and in magnified side view the interdental toothbrush head from FIG. 6 that may be exchanged on any dental shower toothbrush handle from FIG. 6.

FIG. 7 schematically shows in more detail and in magnified view the interdental toothbrush head PNSL from FIG. 6 that may be exchanged on any dental shower toothbrush handle from FIG. 6. The bristle part MZ2 of the toothbrush head, its neck MZ1 and the attachment MZ3 for insertion into the toothbrush handle PN4L, as shown in FIG. 6, are shown here. The shower toothbrush PN2L with thus set or fitted toothbrush head PNSL acts as an interdental toothbrush.

Figure 8:
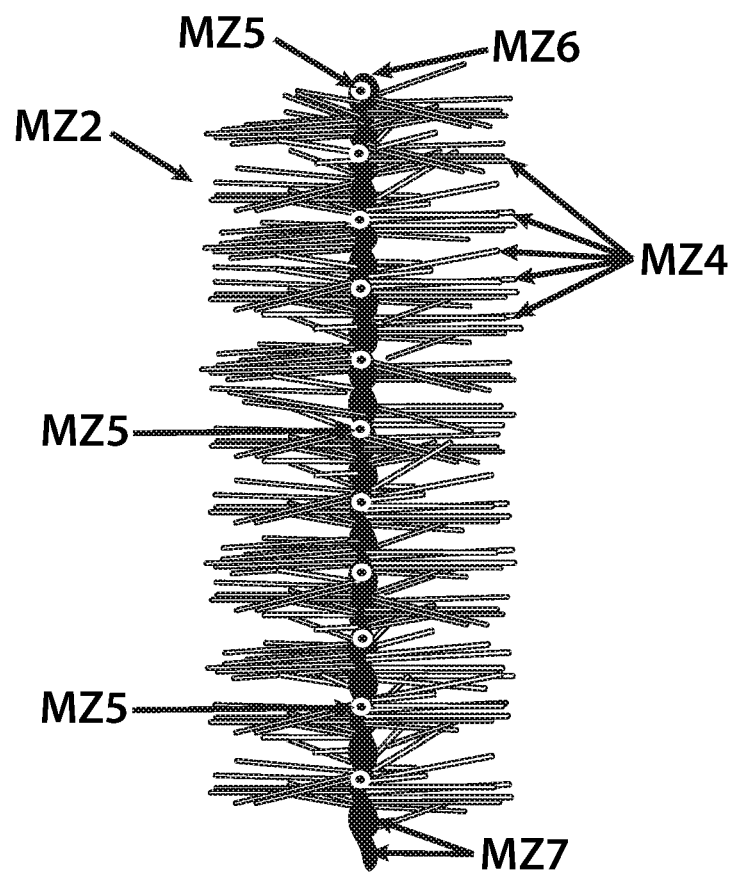
FIG. 8 schematically shows in more detail and in magnified side view the bristle part of the brush, bristles and spray nozzles of the interdental toothbrush head from FIGS. 6 and 7.

FIG. 8 shows in a schematic and magnified view the bristle part MZ2, bristles MZ4 and spray nozzles MZ5 of the interdental toothbrush head PNSL from FIGS. 6 and 7. The bristles MZ4 are supported by the jacket tube MZ7 that curves back at the top of the toothbrush MZ6. This tube may function as the formulation feed tube according to this invention. Alternatively, a separate feed tube may be included inside this jacket tube for feeding the formulation according to this invention to the shower nozzles MZ5.

Figure 9:
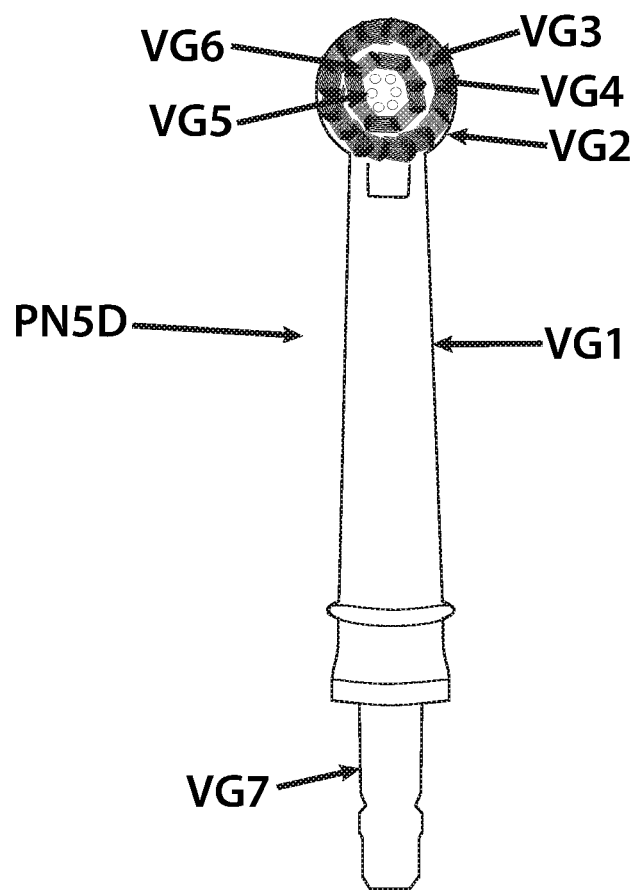
FIG. 9 schematically shows in more detail and in magnified front view the rotating brush head for the oral cavity from FIG. 6 that may be exchanged on any dental shower toothbrush handle from FIG. 6.

FIG. 9 shows in a schematic and magnified front view the rotating toothbrush head PNSD from FIG. 6 and which is used for the oral cavity and that is interchangeably fitted on any brush handle of the dental shower device from FIG. 6. The rotating toothbrush head VG2 has a neck VG1 and a nozzle for insertion into the toothbrush handle PN2D from FIG. 6. The sheaves of bristles VG4 are transversely mounted on the head running along the outer edge of the head, as well as the sheaves of bristles VG6 in the centre of the head to remove impurities from the surfaces of teeth, periodontal tissues (gingiva), tongue and mucous membranes in the oral cavity, as well as spray nozzles VG3 among the sheaves of bristles VG4 and spray nozzles VG5 in the centre of the head. The shower toothbrush PN2D with thus set or fitted rotating toothbrush head PN5D acts as a rotating toothbrush.

Figure 10:
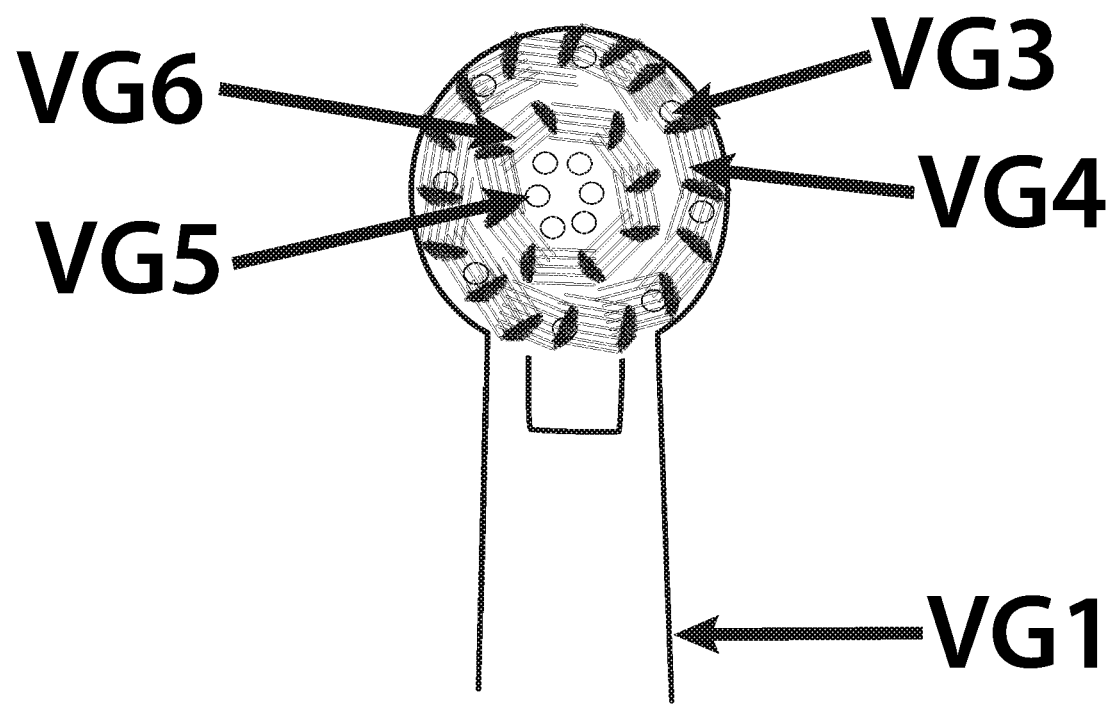
FIG. 10 schematically shows in more detail and in magnified front view the rotating brush head for the oral cavity from FIGS. 6 and 9, its bristles and spray nozzles.

FIG. 10 schematically shows in more detail and in magnified view the rotating toothbrush head PNSD from FIGS. 6 and 9, its bristles VG4 at the outer edge of the head and VG6 in the centre of the head, and the spray nozzles VG3 among the bristles VG4 and the spray nozzles VG5 in the centre of the head.

Figure 11:
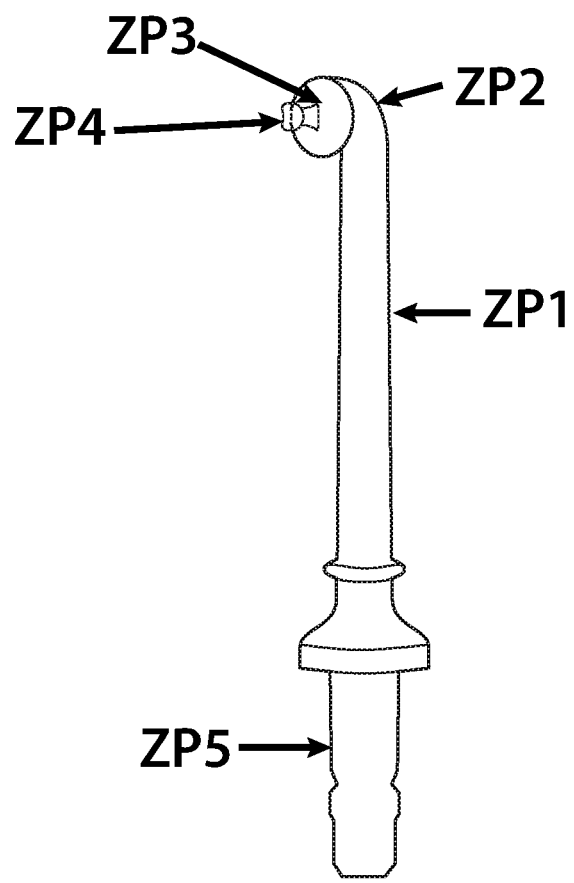
FIG. 11 shows schematically and in zoomed ¾ view the spray brush head that can be exchanged on any toothbrush handle of the dental shower device from FIG. 6.

FIG. 11 schematically and in magnified view shows the spray brush head that can be interchangeably fitted on any brush handle of the dental spray device from FIG. 6. The spray toothbrush has an attachment ZP5 for insertion into the toothbrush handle PN2L or PN2D from FIG. 6 and the neck ZP1 and curve ZP2 and the spray nozzle ZP4 that narrows in funnel form ZP3 from the neck of the head to the spray nozzle ZP4. This toothbrush is designed to clean and rinse your teeth, periodontal and interdental spaces, tongue and other oral cavity structures. When the shower toothbrush PN2L and/or PN2D is fitted with the spray toothbrush head, such toothbrush acts as a spray toothbrush.

The materials for the dental shower device described herein and parts thereof are selected from materials as known in the state of the art. Preferably, these are plastic materials. The tubes may be plastic and, if necessary, of stainless steel, as used in the technical field for medical purposes as for example for injection needles.

Within the scope of the invention as described herein and defined in the following claims, other implementations of formulations with active oxygen compounds that contain the ingredients defined herein and/or their equivalents and other implementations of forms of such formulations and devices that include such formulations for their application on the target area of the organism may be possible, and the processes for their preparation or production with various modifications and variations in the combination of the ingredients described herein, with the various modifications and variations of the forms of formulations and devices described herein, and with the various modifications and variations of the procedures and steps of preparation or production of such formulations described herein, the various forms of such formulations and such devices which include them, since a person skilled in the art may, on the basis of herein described and explained solutions of the technical problem and possible implementations within the meaning of this invention, also develop alternative implementations of such formulations, forms of formulations and devices that include them, but this does not alter the essence of the invention as described and defined herein and defined in the claims.

The invention claimed is:

1. A formulation with active oxygen compounds for maintenance and preservation of a healthy condition of and care for at least one of skin, a tissue, a mucous membrane, a structure of the skin, a system of the skin, a subcutaneous tissue, a fingernail, a toenail, a cuticle, an oral cavity, a system of the oral cavity, a tooth, a periodontal tissue, an interdental space, and their structures and systems, wherein the formulation with active oxygen compounds comprises:
    a composition comprising at least one of: a solution, a gel, an emulsion, a lotion, a milk, a spray, a cream, a mouthwash, a paste, and a film dressing; and
    a controlled delivery structure included within the composition, wherein the controlled delivery structure comprises a nucleus and a hydrophobic portion, wherein a peroxidase enzyme is included in the hydrophobic portion prior to administration of the composition to a patient, and wherein a source of active oxygen compounds is included within the nucleus prior to administration of the composition to the patient;
    wherein the source of active oxygen compounds comprises:
    at least one of hydrogen peroxide, benzoyl peroxide, and carbamide peroxide; and
    at least one of the following:
        (a) silver in colloidal form; and
        (b) gold in colloidal form;
    wherein the peroxidase enzyme provides controlled release of the active oxygen compounds through controlled breakdown of the source of active oxygen compounds after administration of the composition to the patient.

2. The formulation with active oxygen compounds according to claim 1, wherein the source of active oxygen compounds comprises the hydrogen peroxide, and wherein the composition further comprises at least one of the following:
    (a) aloe vera comprising at least one of an extract of leaves of an *Aloe* species of *Aloe barbadensis*, an extract of aloe flowers of the species of *Aloe barbadensis*, a gel that is extruded from leaves of the species of *Aloe barbadensis*, an *Aloe arborescens* leaf extract, and an *Aloe ferox* leaf extract;
    (b) hyaluronic acid; and
    (c) an additional moisturizer comprising at least one of glycerol and propylene glycol.

3. The formulation with active oxygen compounds according to claim 1, wherein the formulation with active oxygen compounds further comprises a stabilizer configured to stabilize the source of active oxygen compounds, wherein the stabilizer comprises at least one of: a sodium pyrophosphate, a colloidal stannate, a colloidal silicate, an organophosphonate, and a phosphoric acid.

4. The formulation with active oxygen compounds according to claim 3, wherein the stabilizer comprises disodium dihydrogen pyrophosphate, and wherein a phosphate ion concentration of the composition does not exceed 0.005 wt. %.

5. The formulation with active oxygen compounds according to claim 1, wherein the formulation with active oxygen compounds further includes a gelling agent comprising at least one of: copolymer of acrylate; polyacrylate cross-polymer 11; ammonium acryloyldimethylaurate; cross polymer of ammonium acryloyldimethylaurate and behenet-25-methacrylate; and hydroxypropyl methylcellulose.

6. The formulation with active oxygen compounds according to claim 1, wherein the formulation with active oxygen compounds further comprises an oil selected from at least one of: olive oil, argan oil, jasmine oil, hemp oil, flaxseed oil, jojoba oil, coconut oil, avocado oil, oils from citrus peel, oranol oil, babassu oil, sunflower oil, and palm oil.

7. The formulation with active oxygen compounds according to claim 2, wherein the hydrogen peroxide is present in a concentration within a range of from and including 0.5 weight % up to and including 6 weight % of the formulation with active oxygen compounds, and wherein the composition further comprises a vitamin selected from at least one of vitamin A, vitamin B, vitamin C, vitamin D, vitamin E, and vitamin K.

8. The formulation with active oxygen compounds according to claim 2, wherein the composition further comprises a mineral selected from magnesium, zinc, and selenium, wherein the mineral is in a form of at least one of a citrate, a chloride, and a carbonate, and wherein the hydrogen peroxide is present in a concentration within a range of from and including 1.5 weight % up to and including 3 weight % of the formulation with active oxygen compounds.

9. The formulation with active oxygen compounds according to claim 2, further comprising an active ingredient comprising an extract from a plant selected from at least one of ginger (*Zingiber Officinale*), purple cornflower (*Echinacea Purpurea*), myrrh (*Commiphora Abyssinica*), marigold (*Calendula Officinalis*), and St. John's wort (*Hypericum perforatum*), and wherein the hydrogen peroxide is present in a concentration of 3 weight % of the formulation with active oxygen compounds.

10. The formulation with active oxygen compounds according to claim 1, wherein the formulation with active oxygen comprises the silver in colloidal form, and wherein the silver in colloidal form is present in a concentration within a range of from and including 0.1 weight % up to and including 4 weight % of the formulation with active oxygen compounds, and further comprising an antioxidant comprising astaxanthin.

11. The formulation with active oxygen compounds according to claim 1, wherein the formulation with active oxygen compounds comprises the gold in colloidal form, and wherein the gold in colloidal form is present in a concentration within a range of from and including 0.1 weight % up to and including 4 weight % of the formulation with active oxygen compounds, and further comprising an essential fatty acid comprising an omega-3 fatty acid.

12. The formulation with active oxygen compounds according to claim 1, wherein the formulation with active oxygen compounds comprises the silver in colloidal form and the gold in colloidal form, and wherein the silver in colloidal form and the gold in colloidal form are simultaneously present in a total concentration within a range of from and including 0.1 weight % up to and including 4 weight % of the formulation with active oxygen compounds, and wherein the composition further comprises at least one of the following:
  (a) hyaluronic acid; and
  (b) an additional moisturizer comprising at least one of glycerol and propylene glycol.

13. The formulation with active oxygen compounds according to claim 1, wherein the composition is configured to be topically applied to a target site of the patient, and wherein at least a portion of the composition is configured to harden when the composition is topically applied to the target site to form a coating.

14. The formulation with active oxygen compounds according to claim 13, wherein a component of the formulation with active oxygen compounds is configured to diffuse into the target site from the coating during an interval of time.

15. The formulation with active oxygen compounds according to claim 14, wherein the interval of time is between 2 minutes and 5 hours.

16. The formulation with active oxygen compounds according to claim 13, wherein an exterior portion of the composition is configured to harden to form the coating when the composition is applied to the target site, and wherein the coating is hydrophobic.

17. The formulation with active oxygen compounds according to claim 13, wherein an inner portion of the composition that is in contact with the target site is hydrophilic.

18. The formulation with active oxygen compounds according to claim 1, wherein the nucleus of the controlled delivery structure further comprises a gel medium.

19. The formulation with active oxygen compounds according to claim 5, wherein the gelling agent is present in a weight concentration within a range of from and including 1 weight % up to and including 5 weight % of the formulation with active oxygen compounds.

20. The formulation with active oxygen compounds according to claim 1, wherein the formulation with active oxygen compounds further comprises glycerine that is present in a weight concentration within a range of from and including 0.2 weight % up to and including 5 weight % of the formulation with active oxygen compounds.

21. The formulation with active oxygen compounds according to claim 1, wherein the controlled delivery structure comprises at least one of:
  (i) a liposome, and
  (ii) a mycelium.

22. The formulation with active oxygen compounds according to claim 1, wherein the peroxidase enzyme comprises at least one of: myeloperoxidase, lactoperoxidase, and horseradish peroxidase.

23. The formulation with active oxygen compounds according to claim 22, wherein the peroxidase enzyme comprises the myeloperoxidase.

24. The formulation with active oxygen compounds according to claim 23, wherein the source of active oxygen compounds further comprises a triethanolamine buffer.

25. A method for producing the formulation with active oxygen compounds according to claim 1, wherein the method includes:
  producing a semi-finished product, where the semi-finished product comprises the formulation with active oxygen compounds and other active ingredients and ingredients prior to being packaged in packaging of different sizes with at least one of different gram and volume contents of the formulation with active oxygen compounds, and wherein the producing the semi-finished product includes:
    filtering and stabilising of the source of active oxygen compounds with stabilisers for nutritional use;
    at least one of dosing and weighing of basic raw material of the hydrogen peroxide into a mixing reactor and continuous stirring with a gradual addition of the active ingredients and ingredients of the formulation with active oxygen compounds to increase a density, wherein ingredients of lesser density are added first and then denser ingredients are added and finally a densest ingredient is added to form the semi-finished product;
    outflowing of the semi-finished product through free fall, where the semi-finished product is drained in the free fall from the mixing reactor into a storage container that is then sealed to prevent access of oxygen, air, and other environmental elements;
    storing the semi-finished product in the storage container until the semi-finished product is filled into the packaging in an environment free of at least one of air, oxygen, other gases, and other environmental elements; and
  b) producing a final product that includes filling the semi-finished product into the packaging.

26. A healthcare formulation for release of active oxygen compounds comprising:
  a composition configured to be applied to an active site of a patient, the composition comprising at least one of: a solution, a gel, an emulsion, a lotion, a milk, a spray, a cream, a mouthwash, a paste, and a film dressing;
  at least one of silver in colloidal form and gold in colloidal form; and
  a controlled delivery structure included within the composition,
  wherein the controlled delivery structure comprises a liposome comprising:
    a phospholipid bilayer comprising an outer hydrophilic membrane lamella, an inner hydrophilic membrane lamella, and a hydrophobic core, wherein the hydrophobic core comprises a peroxidase enzyme embedded within the hydrophobic core prior to administration of the composition to the patient; and
    a nucleus, wherein a source of active oxygen compounds comprising at least one of hydrogen peroxide, benzoyl peroxide, and carbamide peroxide is contained within the nucleus prior to administration of the composition to the patient such that the source of active oxygen compounds is initially separated from the peroxidase enzyme by the inner hydrophilic membrane lamella, wherein at least a portion of the composition is configured to harden to form a coating after the composition is applied to the active site, and wherein the composition is configured to allow ingredients to diffuse from the composition to the active site during a time interval of between 2 minutes and 3 hours after the composition is applied to the active site.

* * * * *